(12) United States Patent
Jalink

(10) Patent No.: US 6,596,499 B2
(45) Date of Patent: Jul. 22, 2003

(54) MEMBRANE MOLECULE INDICATOR COMPOSITIONS AND METHODS

(75) Inventor: Kees Jalink, Heemstede (NL)

(73) Assignee: The Netherlands Cancer Institute, Amsterdam (NL)

(*) Notice: Subject to any disclaimer, the term of this patent is extended or adjusted under 35 U.S.C. 154(b) by 0 days.

(21) Appl. No.: 09/997,956

(22) Filed: Nov. 29, 2001

(65) Prior Publication Data

US 2002/0106714 A1 Aug. 8, 2002

Related U.S. Application Data

(60) Provisional application No. 60/250,679, filed on Nov. 30, 2000, and provisional application No. 60/256,559, filed on Dec. 18, 2000.

(51) Int. Cl.[7] .................. G02N 33/53; C12N 15/00; C12N 15/09; C12N 15/63; C12N 15/70; C12N 15/74; C12N 5/00; C12N 15/02; G01N 21/76; G01N 33/00

(52) U.S. Cl. .................. 435/7.1; 435/7.8; 435/7.9; 435/252.3; 435/320.1; 435/325; 436/86; 436/172; 536/23.5

(58) Field of Search .................. 435/7.1, 7.8, 7.9, 435/252.3, 320.1, 325; 436/86, 172; 536/23.5

(56) References Cited

PUBLICATIONS

Alblas et al., "C–terminal Truncation of the Neurokinin–2 Receptor Causes Enhanced and Sustained Agonist–induced Signaling," *J. Biol. Chem.*, 270(15):8944–8951 (1995).

Alblas et al., "$G_i$–mediated Activation of the $p21^{ras}$–mitogen–activated Protein Kinase Pathway by $\alpha_2$–adrenergic Receptors Expressed in Fibroblasts," *J. Biol. Chem.*, 268(30):22235–22238 (1993).

Alblas et al., "Truncated, Desensitization–defective Neurokinin Receptors Mediated Sustained MAP Kinase Activation, Cell Growth and Transformation by a Ras–independent Mechanism," *EMBO J.*, 15(13):3351–3360 (1996).

Angers et al., "Detection of $\beta_2$–adrenergic Receptor Dimerization in Living Cells Using Bioluminescence Resonance Energy Transfer (BRET)," *Proc. Natl. Sci. USA*, 97(7):3684–3689 (2000).

Balla et al., "Cation Sensitivity of Inositol 1,4,5–Trisphosphate Production and Metabolism in Agonist–stimulated Adrenal Glomerulosa Cells," *J. Biol. Chem.*, 269(23):16101–16107 (1994).

Bottomley et al., "Phospholipid–binding Protein Doamins," *Biochim. Biophys. Acta*, 1436:165–183 (1998).

Conklin et al., "Substitution of Three Amino Acids Switches Receptor Specificity of $G_q\alpha$ to that $G_i\alpha$," *Lett. Nat.*, 363:274–276 (1993).

Delagrave et al., "Red–shifted Excitation Mutants of the Green Fluorescent Protein," *Bio/Technology*, 13:151–154 (1995).

Divecha et al., "The Polyphosphoinositide Cycle Exists in the Nuclei of Swiss 3T3 Cells Under the Control of a Receptor (for IGF–I) in the Plasma Membrane, and Stimulation of the Cycle Increases Nuclear Diacylglycerol and Apparently Induces Translocation of Protein Kinase C to the Nucleus," *EMBO J.*, 10(11):3207–3214 (1991).

(List continued on next page.)

*Primary Examiner*—Kenneth R. Horlick
*Assistant Examiner*—Teresa Strzelecka
(74) *Attorney, Agent, or Firm*—McDermott, Will & Emery

(57) ABSTRACT

The invention provides membrane molecule indicators, including polypeptides, encoding nucleic acid molecules and cells containing such polypeptides and nucleic acid molecules. The invention membrane molecule indicators are characterized in that fluorescence resonance energy transfer (FRET) between a donor fluorescent domain and an acceptor fluorescent domain indicates a property of the membrane molecule. Also provided are methods of using the invention membrane molecule indicators to determine a property of a membrane molecule, and to identify compounds that modulates a property of a membrane molecule.

30 Claims, 10 Drawing Sheets

OTHER PUBLICATIONS

Fradkov et al., "Novel Fluorescent Protein from Discocoma Coral and Its Mutants Possesses a Unique Far–red Fluorescence," *FEBS Letts.*, 479:127–130 (2000).

Gaullier et al., "FYVE Finger Proteins as Effectors of Phosphatidylinositol 3–phosphate," *Chem. Phys. Lip.*, 98:87–94 (1999).

Gether, "Uncovering Molecular Mechanisms Involved in Activation of G Protein–coupled Receptors," *Endocr. Rev.*, 21(1):90–113 (2000).

Griffin et al., "Specific Covalent Labeling of Recombinant Protein Molecules Inside Live Cells," *Science*, 281:269–272 (1998).

Hirose et al., "Spatiotemporal Dynamics of Inositol 1,4,5–Triphosphate that Underlies Complex $Ca^{2+}$ Mobilization Patterns," *Science*, 284:1527–1530 (1999).

Hunyady et al., "Agonist–induced Endocytosis and Signal Generation in Adrenal Glomerulosa Cells," *J. Biol. Chem.*, 266(5):2783–2788 (1991).

Jalink and Moolenaar, "Thrombin Receptor Activation Causes Rapid Neural Cell Rounding and Neurite Retraction Independent of Classic Second Messengers," *J. Cell Biol.*, 118(2):411–419 (1992).

Jalink et al., "Lysophosphatidic Acid Induces Neuronal Shape Changes via a Novel Receptor–mediated Signaling Pathway: Similarity to Thrombin Action," *Cell Gr. Diff.*, 4:247–255 (1993).

Janetopoulos et al., "Receptor–mediated activation of Heterotrimeric G–proteins in Living Cells," *Science* 291:2408–2411 (2001).

Janmey, "Protein Regulation by Phosphatidylinositol Lipids," *Chem. Biol.*, 2(2):61–65 (1995).

Komatsuzaki et al., "A Novel System that Reports the G–proteins Linked to a Given Receptor: A Study of Type 3 Somatostatin Receptor," *FEBS Lett.*, 406:165–170 (1997).

Kranenburg et al., "Activation of RhoA by Lysophosphatidic Acid and $G\alpha_{12/13}$ Subunits in Neuronal Cells: Induction of Neurite Retraction," *Mol. Biol. Cell*, 10:1851–1857 (1999).

Lemmon et al., "Specific and High–affinity Binding of Inositol Phosphate to an Isolated Pleckstrin Homology Domain," *Proc. Natl. Acad. Sci. USA*, 92:10472–10476 (1995).

Miyawaki et al., "Fluorescent Indicators for $Ca^{2+}$ Based on Green Fluorescent Proteins and Calmodulin," *Lett. Nat.*, 388:882–887 (1997).

Myers and Larkins, "Bradykinin–induced Changes in Phosphoinositides, Inositol Phosphate Production and Intracellular Free Calcium in Cultured Bovine Aortic Endothelial Cells," *Cell. Sign.*, 1(4):335–343 (1989).

Nalefski and Falke, "The C2 Domain Calcium–binding Motif: Structural and Functional Diversity," *Science*, 5(12):2375–2390 (1996).

Newton et al., "Angiogenin Single–chain Immunofusions: Influence of Peptide Linkers and Spacers Between Fusion Protein Domains," *Biochemistry*, 35:545–553 (1996).

Paltauf–Doburzynska et al., "Hitsamine–induced $Ca^{2+}$ Oscillations in a Human Endothelial Cell Line Depend on Transmembrane Ion Flux, Ryanodine Receptors and Endoplasmic Reticulum $Ca^{2+}$–ATPase," *J. Phys.*, 524.3:701–713 (2000).

Pollok and Heim, "Using GFP in FRET–based Applications," *Cell Biol.*, 9:57–60 (1999).

Ponting and Aravind, "Start: A Lipid–binding Domain in StAR, HD–ZIP and Signaling Proteins," *TIBS*, 24:130–132 (1999).

Rebecchi and Scarlata, "Pleckstrin Homology Domains: A Common Fold with Diverse Functions," *Annu. Rev. Biophys. Biomol. Struct.*, 27:503–528 (1998).

Shayman, "Sphingolipids," *Kidn Inter.*, 58:11–26 (2000).

Stauffer et al., "Receptor–induced Transient Reduction in Plasma Membrane PtdIns $(4,5)P_2$ Concentration Monitored in Living Cells," *Curr. Biol.*, 8:343–346 (1998).

Stenmark and Aasland, "FYVE–finger Proteins—Effectors of an Inositol Lipids," *J. Cell Sci.*, 112:4175–4183 (1999).

Stephens et al., "Activation of Phosphatidylinositol 4,5–bisphosphate Supply by Agonists and Non–Hydrolysable GTP Analogues," *Biochem. J.*, 296:481–488 (1993).

Tall et al., "Dynamics of Phosphatidylinositol 4,5–bisphosphate in Actin–rich Structures," *Curr. Biol.*, 10:743–746 (2000).

Tilly et al., "Epidermal–growth–factor–induced Formation of Inositol Phosphate in Human A431 Cells," *Biochem. J.*, 252:857–863 (1988).

Tilly et al., "Histamine–$H_1$–receptor–mediated Phosphoinositide Hydroysis, $Ca^{2+}$ Signalling and Membrane–potential Oscillations in Human HeLa Carcinoma Cells," *Biochem. J.*, 266:235–243 (1990).

Tsien, "The Green Fluorescent Protein," *Annu. Rev. Biochem.*, 67:509–544 (1998).

Van der Bend et al., "The Biologically Active Phospholipid, Lysophosphatidic Acid, Induces Phosphatidylcholine Breakdown in Fibroblasts via Activation of Phospholipase D," *Biochem. J.*, 285:235–240 (1992).

Van der Wal, "Monitoring Agonist–induced Phospholipase C Activation in Live Cells by Fluorescence Resonance Energy Transfer," *J. Biol. Chem.*, 4;276(18):15337–15344 (2001).

Van Leeuwen et al., "Rac Regulates Phosphorylation of the Myosin–II Heavy Chain, Actinomyosin Disassembly and Cell Spreading," *Nat. Cell Biol.*, 1:242–248 (1999).

Verveer et al., "Global Analysis of Fluorescence Lifetime Imaging Microscopy Data," *Biophys. J.*, 78:2127–2137 (2000).

Vollmer et al., "Subcellular Compartmentalization of Activation and Desensitization of Responses Mediated by NK2 Neurokinin Receptors," *J. Biol. chem.*, 274(53):37915–37922 (1999).

Weidemann et al., "Chromaffin Granule–Associated Phosphatidylinositol 4–kinase Activity is Required for Stimulated Secretion," *EMBO J.*, 15 (9):2094–2101 (1996).

Wijelath et al., "Interleukin–one Induced Inositol Phospholipid Breakdown in Murine Macrophages: Possible Mechanism of Receptor Activation," *Biochem. Biophys. Res. Comm.*, 152(1):392–397 (1988).

Winzor, "From Gel Filtration to Biosensor Technology: The Development of Chromatography for the Characterization of Protein Interactions," *J. Mol. Recog.*, 13:279–298 (2000).

Xu et al., "A Bioluminiscence Resonance Energy Transfer (BRET) System: Application to Interacting Circadian Clock Proteins," *Proc. Natl. Acad. Sci. USA*, 96:151–156 (1999).

Zhang et al., "Inhibition by Toxin B of Inositol Phophate

Formation Induced by G Protein–coupled and Tyrosine Kinase Receptors in N1E–115 Neuroblastoma Cells: Involvement of Rho Proteins," *Mol. Pharmacol.*, 50:864–869 (1996).

Zhu et al., "Inositol Tetrakisphosphate as a Frequency Regulator in Calcium Oscillations in HeLa Cells," *J. Biol. Chem.*, 275(9):6063–6066 (2000).

Bastiaens and Jovins, "Microspectroscopic imaging tracks the intracellular processing of a signal transduction protein: Fluorescent–labeled protein kinase C βI," *Proc. Natl. Acad. Sci. USA* 93:8407–8412 (1996).

Broudy et al., "Analysis of c–kit Receptor Dimerization by Fluorescence Resonance Energy Transfer," *Blood* 91:898–906 (1998).

Kenworthy and Edidin, "Distribution of a Glycosylphosphatidylinositol–anchored Protein at the Apical Surface of MDCK Cells Examined at a Resolution of <100 Å Using Imaging Fluorescence Resonance Energy Transfer," *The Journal of Cell Biology* 142:69–84 (1998).

Sorkin et al., "Interactions of EGF receptor and Grb2 in living cells visualized by fluorescence resonance energy transfer (FRET) microscopy," *Current Biology* 10:1395–1398 (2000).

Wouters and Bastiaens, "Fluorescence lifetime imaging of receptor tyrosine kinase activity in cells," *Current Biology* 9:1127–1130 (1999).

SEQUENCE LISTING

```
<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: synthetic construct
<221> NAME/KEY: VARIANT
<222> LOCATION: 2
<223> OTHER INFORMATION: Xaa=R or K
<221> NAME/KEY: VARIANT
```

<222> LOCATION: 7
<223> OTHER INFORMATION: Xaa=any amino acid

<400> SEQUENCE: 1

Arg Xaa His His Cys Arg Xaa Cys Gly
 1               5

<210> SEQ ID NO 2
<211> LENGTH: 4
<212> TYPE: PRT
<213> ORGANISM: Homo sapiens

<400> SEQUENCE: 2

Lys Asp Glu Leu
 1

<210> SEQ ID NO 3
<211> LENGTH: 42
<212> TYPE: DNA
<213> ORGANISM: Artificial Sequence
<220> FEATURE:
<223> OTHER INFORMATION: primer

<400> SEQUENCE: 3
cctgcggccg cggtaccgat atcagatgtt gagctccttc ac         42

<210> SEQ ID NO 4
<211> LENGTH: 42
<212> TYPE: DNA
<213> ORGANISM: Artificial Sequence
<220> FEATURE:
<223> OTHER INFORMATION: primer

<400> SEQUENCE: 4
ccgaattccc gggtctcagc catggactcg ggccgggact tc         42

<210> SEQ ID NO 5
<211> LENGTH: 40
<212> TYPE: DNA
<213> ORGANISM: Artificial Sequence
<220> FEATURE:
<223> OTHER INFORMATION: primer

<400> SEQUENCE: 5
ggctgagacc cgggaattcg gcttgtacag ctcgtccatg            40

<210> SEQ ID NO 6
<211> LENGTH: 20
<212> TYPE: PRT
<213> ORGANISM: Homo sapiens

<400> SEQUENCE: 6

Lys Met Ser Lys Asp Gly Lys Lys Lys Lys Lys Ser Lys Thr Lys
 1               5                  10                  15

Cys Val Ile Met
            20

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7

-continued

```
ccgaattccc gggtcaagat gagcaaagat ggtaaaaag                    39

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
cctgcggccg cggtaccgag atctttacat aattacacac tt               42
```

MEMBRANE MOLECULE INDICATOR COMPOSITIONS AND METHODS

This application claims the benefit of U.S. Provisional Application No. 60/250,679, filed Nov. 30, 2000, and U.S. Provisional Application No. 60/256,559, filed Dec. 18, 2000, which are both incorporated herein by reference.

BACKGROUND OF THE INVENTION

The invention relates generally to the field of signal transduction and, more specifically, to compositions and methods for indicating properties of membrane molecules using fluorescence resonance energy transfer (FRET).

The transduction of signals from the outside to the inside of a cell underlies most cellular processes, including proliferation, differentiation, apoptosis, motility and invasion. Therefore, there is considerable interest in developing improved methods of monitoring signal transduction in response to normal and abnormal stimuli. Methods of monitoring signal transduction have numerous applications, such as in identifying or improving modulators of signal transduction pathways, which are candidate therapeutic drugs or therapeutic targets, and in detecting pathological alterations in cells.

Some of the earliest and most sensitive signals transduced in response to stimuli involve changes in properties of membrane molecules, including membrane lipids and polypeptides, such as changes in location, abundance, conformation or post-translational modification state. Accordingly, there exists a need to develop compositions and methods suitable for indicating changes in properties of membrane molecule.

An early response to agonist stimulation of many tyrosine kinase and G-protein coupled receptors is the activation of the enzyme phospholipase C, which cleaves the lipid phosphatidylinositol 4,5-bisphosphate (PIP2) to generate second messengers that increase cytosolic free $Ca^{2+}$ concentration. Although $Ca^{2+}$ indicators and methods have been described that allow monitoring of $Ca^{2+}$ concentration in single living cells with high spatial and temporal resolution, $Ca^{2+}$ fluxes, being more distal to receptor activation, may not as faithfully report receptor activation levels as changes in PIP2 levels.

In a recently developed method for detecting PIP2 dynamics in living cells, a pleckstrin homology (PH) domain tagged with a green fluorescent protein (GFP) has been used. Detection of PIP2 hydrolysis was by in vivo visualization, such as by confocal imaging and post acquisition image analysis, of translocation of the fluorescence from the membrane to the cytosol. However, this method suffers from several disadvantages. First, it is hard to obtain quantitative data using confocal microscopy, since even minor focal drift and changes in cell morphology that often occur after stimulation render quantitative measurements unreliable. Second, it is difficult to visualize translocation in very flat cells or in cellular subregions. Third, at fast imaging rates, confocal imaging requires high excitation intensities that can cause severe cell damage in minutes. Fourth, the imaging approach is not easily extended to cell populations. Therefore, there exists a need to develop improved methods for detecting PIP2 dynamics in cells, and particularly methods amenable to high-throughput screening.

The present invention satisfies these needs and provides related advantages as well.

SUMMARY OF THE INVENTION

The invention provides a phosphatidylinositol 4,5-bisphosphate (PIP2) indicator. The indicator contains:

(a) a first polypeptide having:
  (i) a pleckstrin homology (PH) domain; and
  (ii) a donor fluorescent domain
(b) a second polypeptide having:
  (i) a pleckstrin homology (PH) domain; and
  (ii) an acceptor fluorescent domain;
wherein fluorescence resonance energy transfer (FRET) between the donor domain and the acceptor domain indicates PIP2 levels.

Also provided is a nucleic acid kit, the nucleic acid molecule components of which encode a PIP2 indicator, the indicator containing:

(a) a first polypeptide having:
  (i) a PH domain; and
  (ii) a donor fluorescent domain
(b) a second polypeptide having:
  (i) a PH domain; and
  (ii) an acceptor fluorescent domain;
wherein fluorescence resonance energy transfer (FRET) between the donor domain and the acceptor domain indicates PIP2 levels.

Further provided is a method of indicating PIP2 levels in a cell. The method includes the steps of:

(a) providing a cell containing a PIP2 indicator; and
(b) determining FRET between the donor fluorescent domain and the acceptor fluorescent domain, wherein FRET between the donor domain and the acceptor domain indicates PIP2 levels in the cell.

The invention also provides a method of identifying a compound that modulates PIP2 levels in a cell. The method includes the steps of:

(a) contacting a cell containing a PIP2 indicator with one or more test compounds; and
(b) determining FRET between the donor fluorescent domain and the acceptor fluorescent domain following the contacting,
wherein increased or decreased FRET following contacting indicates that the test compound is a compound that modulates PIP2 levels in the cell.

DETAILED DESCRIPTION OF THE INVENTION

The invention provides membrane molecule indicator compositions, including polypeptides, encoding nucleic acid molecules, and cells, as well as related methods for determining properties of a membrane molecule and for identifying modulatory compounds.

The membrane molecule indicator compositions of the invention are characterized by a membrane molecule indicator domain, a donor fluorescent domain and an acceptor fluorescent domain. The donor fluorescent domain and acceptor fluorescent domain exhibit a characteristic fluorescence resonance energy transfer (FRET) when the membrane molecule indicator domain is associated with a membrane molecule at a membrane. This characteristic FRET observed when the membrane molecule indicator domain and membrane molecule are associated at the membrane differs from FRET observed when the membrane molecule indicator domain dissociates from the membrane molecule, or when the membrane molecule is no longer localized to the membrane. Therefore, FRET between the donor and acceptor fluorescent domains serves as an indicator of association at the membrane between the membrane molecule indicator domain and the membrane molecule, and thus serves as an indicator of a property of the membrane molecule.

In one embodiment, FRET is high when the membrane molecule indicator domain and membrane molecule are associated at the plasma membrane (e.g. FIGS. 1A–D and FIG. 9, top), and low when the membrane molecule indicator domain dissociates from the membrane molecule (e.g. FIGS. 1E–H), or when the membrane molecule relocalizes (e.g. FIGS. 1I–L and FIG. 9, bottom).

Figure 10:
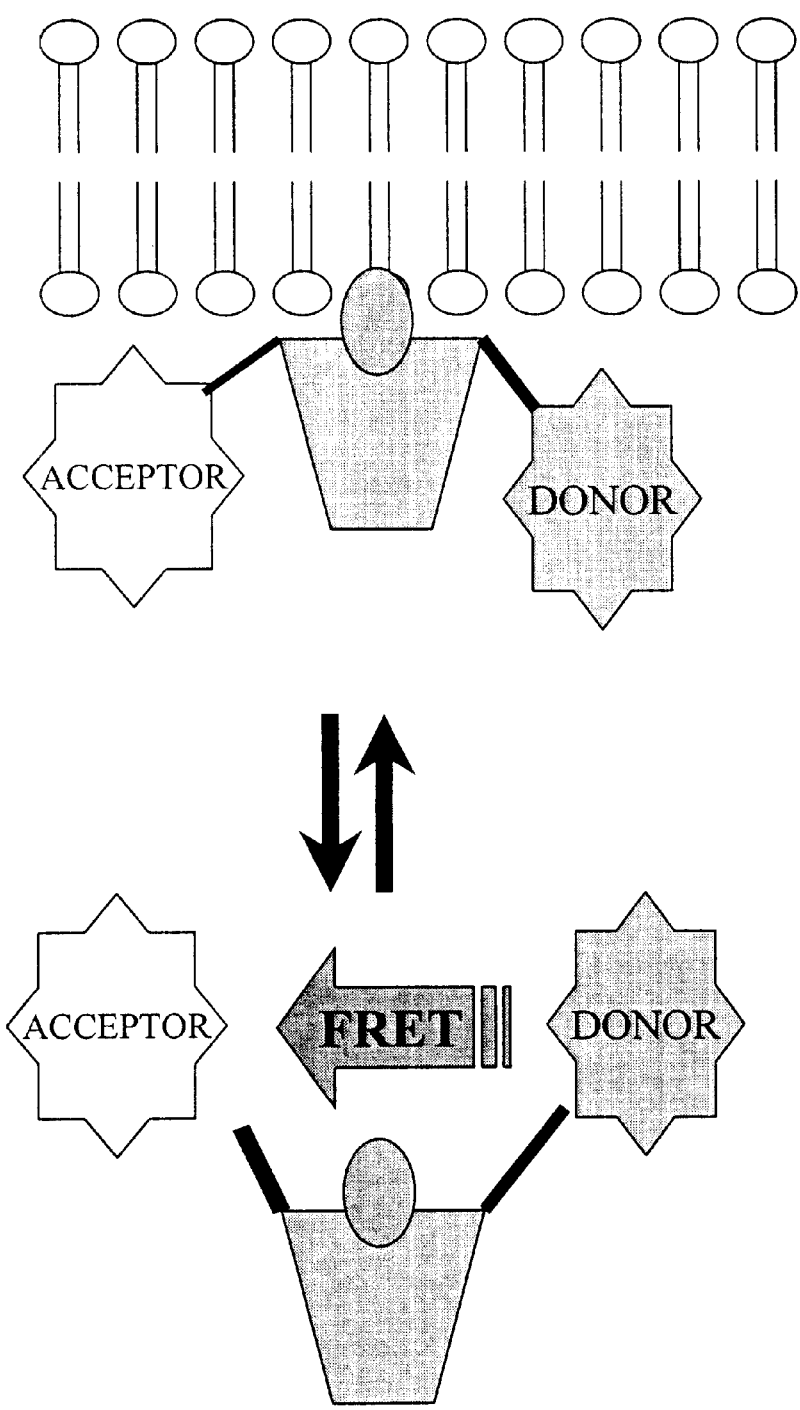
FIG. 10 shows an exemplary membrane molecule indicator. Oval: membrane molecule. Trapezoid: MMID. The donor and acceptor fluorescent domains are indicated. Top: FRET is low due to association between MMID and the membrane molecule at the membrane and separation of the donor and acceptor. Bottom: FRET is high due to relocalization of membrane molecule and resulting proximity of the donor and acceptor.

In another embodiment, FRET is low when the membrane molecule indicator domain and membrane molecule are associated at the plasma membrane (e.g. FIG. 10, top), and high when the membrane molecule indicator domain dissociates from the membrane molecule, or when the membrane molecule relocalizes (e.g. FIG. 10, bottom).

Properties of a membrane molecule that can affect its ability to associate at the membrane with an indicator domain include, for example, its localization, abundance, conformation and post-translational modifications. These properties of membrane molecules are of considerable interest, as they often reflect changes that occur as a result of activation or inactivation of cellular signaling pathways that regulate fundamental cellular processes, including growth, differentiation, apoptosis, motility and invasion. Therefore, the invention compositions and methods can be used to identify and determine the function of modulators of cellular signaling pathways, and thus have important therapeutic, diagnostic and research applications.

In one embodiment, the membrane molecule indicator compositions of the invention contain (or encode) a single polypeptide that contains a membrane molecule indicator domain, a membrane anchor, a donor fluorescent domain and an acceptor fluorescent domain (shown schematically in FIG. 1A).

In an alternative embodiment, the membrane molecule indicator compositions of the invention contain (or encode) two polypeptides, one containing a membrane molecule indicator domain, the other containing a membrane anchor domain, one of which further contains a donor fluorescent domain, the other of which further contains an acceptor fluorescent domain (shown schematically in FIG. 1B).

In another embodiment, the membrane molecule indicator compositions of the invention contain (or encode) a single polypeptide that contains two membrane molecule indicator domains, a donor fluorescent domain and an acceptor fluorescent domain (shown schematically in FIG. 1C).

In yet another embodiment, the membrane molecule indicator compositions of the invention contain (or encode) two polypeptides, each containing a membrane molecule indicator domain, one of which contains a donor fluorescent domain and the other of which contains an acceptor fluorescent domain (shown schematically in FIG. 1D).

Figure 9:
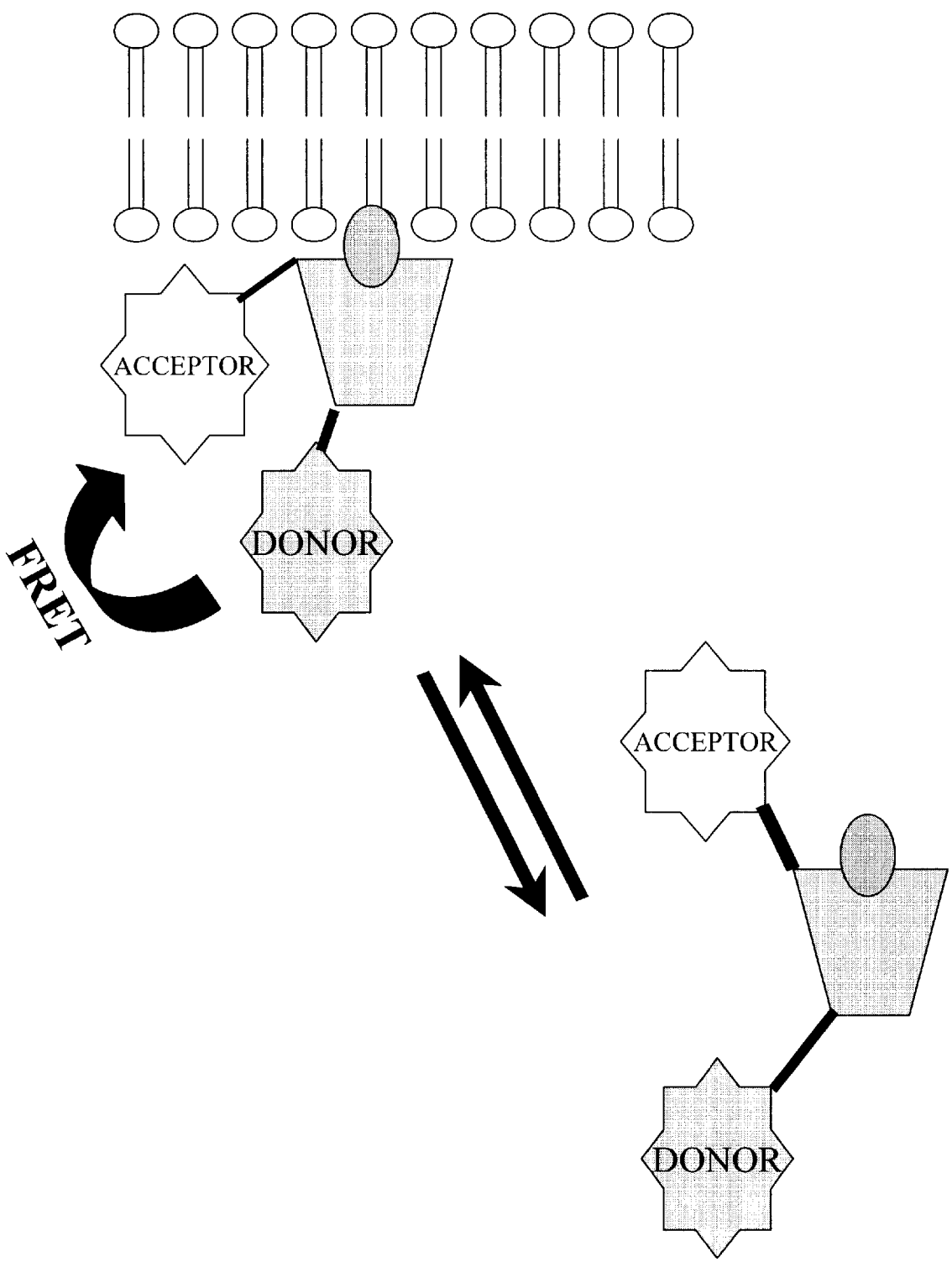
FIG. 9 shows an exemplary membrane molecule indicator. Oval: membrane molecule. Trapezoid: MMID. The donor and acceptor fluorescent domains are indicated. Top: FRET is high due to association between MMID and the membrane molecule at the membrane and proximity of the donor and acceptor. Bottom: FRET is low due to relocalization of membrane molecule and resulting separation of the donor and acceptor.

In a further embodiment, the membrane molecule indicator compositions of the invention contain (or encode) one polypeptide, containing a central membrane molecule indicator domain, with a donor fluorescent domain and an acceptor fluorescent domain at the termini (shown schematically in FIGS. 9 and 10).

Figure 1:
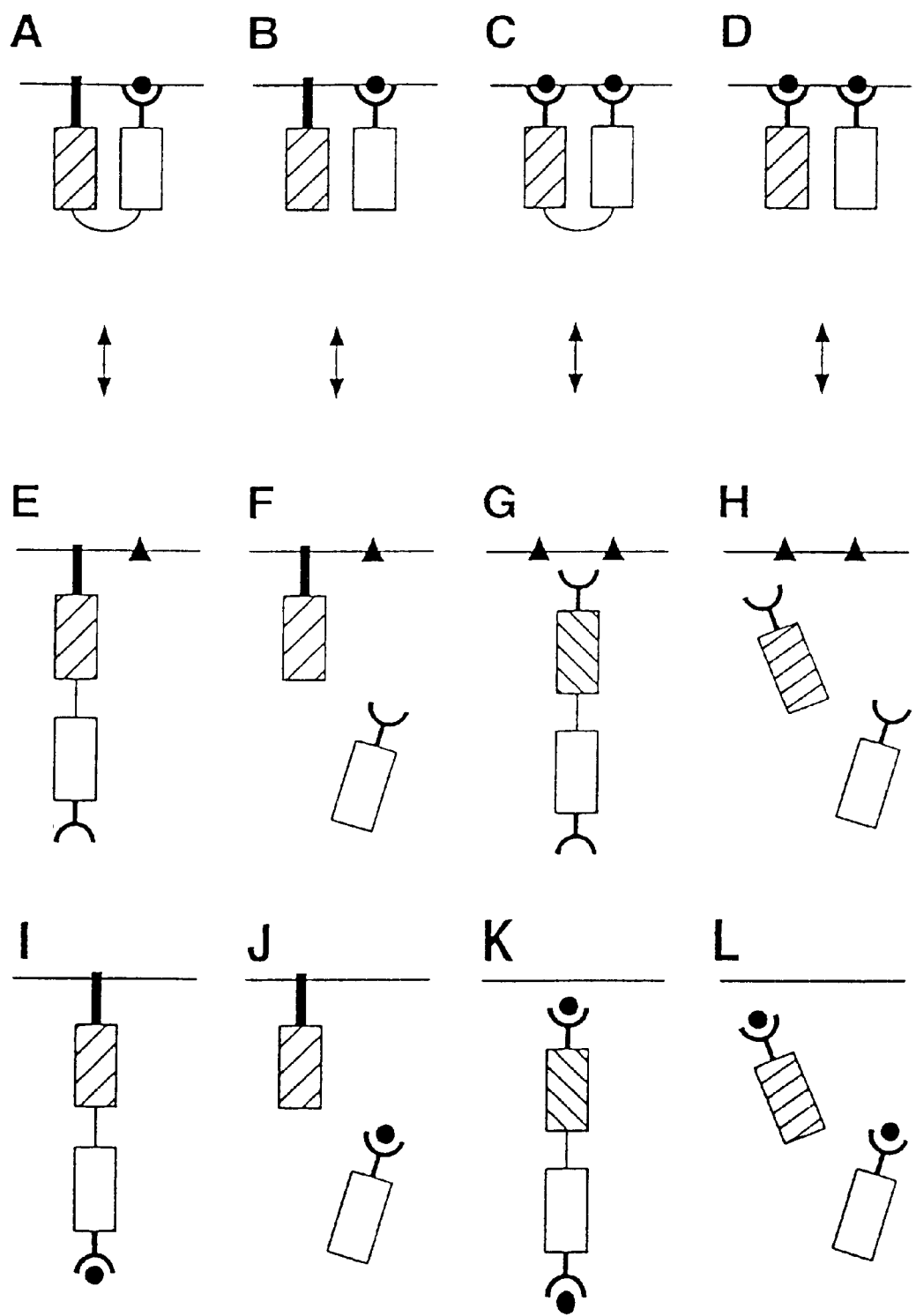
FIGS. 1A–L shows four exemplary membrane molecule indicator compositions. Solid bar: membrane anchoring domain. Hatched and open boxes: fluorescent donor domain or fluorescent acceptor domain. Thick semi-circle: MMID. Thin semi-circle: linker. Solid circle: membrane molecule. Solid triangle: represents an altered property of membrane molecule. (A–D): FRET is high due to association between membrane molecule indicator domain (MMID) and membrane molecule at the membrane. (E–H): FRET is low due to dissociation between MMID and membrane molecule, as a result of an altered property of membrane molecule. (I–L): FRET is low due to altered localization of membrane molecule.

It will be appreciated by the skilled person that the membrane molecule indicators shown in FIGS. 1, 9 and 10 can be modified in a variety of ways, so long as the donor and fluorescent domains are operably positioned so as to exhibit a characteristic FRET when the membrane molecule indicator domain and membrane molecule are associated at the membrane, which differs from FRET observed when the membrane molecule indicator domain dissociates from the membrane molecule, or when the membrane molecule is no longer localized to the membrane.

For example, the relative locations of the donor fluorescent domain and acceptor fluorescent domain with respect to a membrane anchoring domain can be reversed in the compositions shown in FIGS. 1A and B. The membrane molecule indicator compositions can also contain additional peptide or non-peptide domains, such as linker sequences between the donor fluorescent domain and acceptor fluorescent domain, or between a fluorescent domain and either the MMID or the membrane anchor. Likewise, either the donor or acceptor fluorescent domains shown in FIGS. 9 and 10 can optionally contain membrane anchor domains.

When two MMIDs are present, the MMIDs can each associate with the same type of membrane molecule. In such applications, the MMIDs can be identical, or different, so long as they associate with the same type of membrane molecule. For other applications, it may be preferable that the MMIDs associate with different types of membrane molecules, which are commonly or differentially regulated. Thus, such the membrane molecule indicator compositions can simultaneously, or alternatively, report the properties of two different membrane molecules.

As used herein, the term "membrane molecule" refers to a molecule that transiently, or permanently, resides at, partially or completely within, or across, a lipid bilayer of a cell. A membrane molecule can thus be an integral membrane molecule, such as a lipid bilayer component or an integral membrane protein. Alternatively, a membrane molecule can be a peripheral membrane molecule that directly associates with the lipid bilayer, or indirectly associates with the lipid bilayer by virtue of interaction with an integral membrane molecule.

A membrane molecule useful in the methods of the invention is a molecule that as a direct or indirect response to a normal or pathological stimulus, exhibits a change in a property that results in an increased or decreased association at the membrane between the membrane molecule and the particular membrane molecule indicator domain.

Exemplary properties of a membrane molecule that can change in response to a stimulus, and which can result in an increased or decreased association at the membrane between the membrane molecule and the MMID, include location (e.g. translocation of the membrane molecule from its membrane location to a different cellular location, or vice versa), abundance (e.g. local, or overall, increase or decrease in abundance of the membrane molecule at the membrane), conformation (e.g. tertiary or quaternary structure, which can reflect activation state), and post-translational modification state (e.g. acylation, biotinylation, mannosylation, farnesylation, formylation, geranyl-geranylation, hydroxylation, methylation, myristoylation, palmitoylation, phosphorylation, sulphation and the like). Therefore, such properties of a membrane molecule, as indicated by its relative ability to associate with a membrane molecule indicator domain, reflect the presence and nature of the stimulus. The appropriate property which changes in response to a stimulus, will depend on the nature of the membrane molecule and the stimulus.

As an example of a class of membrane molecules that exhibit changes in properties in response to stimuli, it is well known in the art that tyrosine kinase receptors often exhibit changes in location and abundance at the membrane (e.g. by becoming internalized), conformation (e.g. by adopting an activated tertiary conformation, dimerizing, or associating with effector molecules), and/or post-translational state (e.g. by becoming tyrosine phosphorylated) in response to ligands. Certain phospholipids exhibit changes in abundance (e.g. by becoming hydrolyzed or produced) in response to agonist activation of receptors. Other examples of membrane molecules and changes in their properties in response to stimuli, which can be detected using the methods and compositions of the invention, are known in the art and described further below.

As used herein, the term "membrane," with respect to the location of a membrane molecule detected by the indicator compositions of the invention, refers to any lipid bilayer of a cell, including, but not limited to, the plasma membrane, Golgi membrane, endoplasmic reticulum (ER) membrane, mitochondrial membrane, endosomal membrane, peroxisomal membrane, lysosomal or vacuolar membrane, and nuclear membrane.

A membrane molecule can be of any nature, such as a lipid, protein, saccharide, or any combination thereof. In one embodiment, the membrane molecule is a membrane lipid. Exemplary membrane lipids include cholesterol, sphingolipids, polyisoprenoids, mono-, di- and triacylglycerols, acyl chains and their derivatives (e.g. arachadonic acid and its metabolites, such as prostaglandins), and phospholipids (e.g. phosphatidylcholine, phosphatidylserine, phosphatidylethanolamine, phosphatidic acid, phosphaytidlyglycerols, lyso-derivatives thereof and phosphatidylinositols. Exemplary phosphatidylinositols include PtdIns $(4, 5)P_2$ (also referred to as PIP2), PtdIns $(3, 4) P_2$, PtdIns $(3, 4, 5) P_3$, PtdIns, PtdIns $(3) P$, PtdIns $(4)P$, as well as D-enantiomers (e.g. D-Ins $(1, 4, 5) P_3$), di-carboxy derivatives (e.g. $DiC_8$-PtdIns $(4, 5)P_2$) and glycerophosphoryl derivatives (e.g. g-PtdIns $(4, 5)P_2$)of these molecules.

The structural and regulatory function of membrane lipids in normal and abnormal biological processes, as well as the changes in properties of lipids (e.g. abundance, localization, conformation and post-translation modifications) that occur in response to normal and pathological stimuli, are well known in the art.

For example, a variety of sphingolipids have roles in signaling, such as sphingosine in inhibiting PKC, ceramide in modulating arachidonic acid (AA) release, and sphingosine-1-phosphate in mobilizing calcium (reviewed in Shayman, *Kidney International* 58:11–26 (2000). As other examples of the role of membrane lipids in signaling, diacylglycerol (DAG) activates protein kinase C (PKC); phosphatidic acid (PA) activates certain kinases; and phosphatidyl choline serves as a substrate for phospholipase D to generate PA and then DAG, as well as a substrate for phospholipase A2 to generate AA, which is the precursor for eicosanoids and prostaglandins.

Phosphatidylinositols are particularly important signaling molecules. For example, many cell surface receptors are coupled to phospholipase C activation. PLC activation cleaves the phosphatidylinositol PIP2 to produce the second messengers inositol 1,4,5-trisphosphate (IP3) and diacylglycerol (DAG). These second messengers increase intracellular $Ca^{2+}$ concentration and activate the serine/threonine specific protein kinase C (PKC), respectively. PIP2 also serves as a substrate for phosphatidyl inositol 3-kinase (PI3K), producing the second messenger phosphatidylinositol (3,4,5)-trisphosphate (PIP3). PIP2 also is implicated in the regulation of the actin cytoskeleton, based on its ability to bind to and regulate the function of a number of actin severing, capping and bundling proteins. Additionally, PIP2 modulates the activity of phospholipase D (PLD), which catalyzes the hydrolysis of phosphatidylcholine to phosphatidic acid and choline.

PIP2 resides at the plasma membrane of resting cells. Upon agonist stimulation of a receptor coupled to PLC, such as a tyrosine kinase receptor, or a G-protein coupled receptor (GPCR) that acts through a Gαq-containing effector G protein, PIP2 is hydrolyzed to yield soluble IP3 and membrane bound DAG. PIP2 is then resynthesized and returns to the membrane. Accordingly, the abundance of PIP2 at the plasma membrane reports the activation state of a PLC-coupled receptor, in that high abundance of PIP2 at the plasma membrane indicates the resting state, and low abundance indicates agonistic activity through the receptor.

In an alternative embodiment, a membrane molecule is a membrane protein. Exemplary membrane proteins include integral membrane proteins such as cell surface receptors (e.g. G-protein coupled receptors (GPCRs), tyrosine kinase receptors, integrins and the like) and ion channels; and proteins that shuttle between the membrane and cytosol in response to signaling (e.g. Ras, Rac, Raf, Gα subunits, arresting, Src and other effector proteins). In certain embodiments, when specifically indicated, excluded from the scope of the invention is a membrane molecule that is a GPCR.

The structural and regulatory function of membrane proteins in normal and abnormal biological processes, as well as the changes in their properties (e.g. abundance, localization, conformation and post-translation modifications) that occur in response to normal and pathological stimuli, are well known in the art.

As used herein, a "membrane molecule indicator domain" or "MMID" refers to a domain that associates with a membrane molecule with sufficient affinity and selectivity to report a property of the membrane molecule. The choice of membrane molecule indicator domain will depend on the particular membrane molecule. MMIDs for the membrane molecules described above are known in the art, or can be readily determined. Suitable MMIDs include, for example, domains that mediate interaction with the membrane molecule that are present in its naturally occurring oligomeric partner(s), regulators and effectors, as well as functional variants of such domains. Thus, for example, MMIDs that bind to membrane molecules can consist of SH2, SH3, PH, PTB, EH, PDZ, EVH1 and WW domains that bind the membrane molecule in vivo, as well as functional variants of such domains.

In certain embodiments, such as when the membrane molecule indicator is designed to indicate activation state of a GPCR, the MMID can comprise a G-protein subunit, such as a Gα, Gβ or Gγ subunit. For example, high FRET between a Gα subunit linked to a donor fluorescent domain and a Gβ and/or Gγ subunit linked to an acceptor fluorescent domain (or vice versa) can indicate the inactive state of the GPCR, in which the trimeric G-protein complex is present at the membrane. In contrast, low FRET can indicate activation of the GPCR and dissociation of the G-protein complex. In other embodiments, when specifically indicated, excluded from the scope of the invention is an MMID which comprises a G-protein subunit.

MMIDs also include domains which do not normally interact with the membrane molecule in the cell, but are determined, by methods known in the art, to have sufficient affinity and selectivity to report a property of the membrane molecule.

Where the membrane molecule is a phosphatidylinositol, a suitable membrane molecule indicator domain is a phosphatidylinositol binding domain. Phosphatidylinositol binding domains include, for example, "pleckstrin homology" or "PH" domains, "FYVE" domains, "C2" domains, "SH2" domains, PtdIns-binding domains of actin-binding proteins, PtdIns-binding domains of clathrin adaptor proteins, and START domains (reviewed in Bottomley et al., *Bioc. Biophys. Acta* 1436:165–183 (1998); Stenmark et al., *J. Cell Science* 112:4175–4183 (1999); Janmey, *Chem. Biol.* 2:61–65 (1995); and Ponting et al., *TIBS* 24:130–132 (1999)).

In one embodiment, the phosphatidylinositol indicator domain is a pleckstrin homology (PH) domain. PH domains are generally around 120 amino acids long and share characteristic structural features that include two orthogonal β-sheets of three and four anti-parallel β-strands, which sandwich an α-helix at the C-terminus. PH domains also contain clusters of lysine and arginine residues distal to the C-terminal α-helix that create a highly charged surface, and an almost invariant tryptophan residue near the C-terminus. PH domains have been found in more than 100 different proteins, including mammalian, Drosophila, *C. elegans* and yeast proteins. Many PH domain containing proteins are involved in intracellular signaling and cytoskeletal organization.

Examples of PH domain containing proteins include protein kinases (e.g. Btk, β-ARK and Akt), all phospholipase C (PLC) isoforms (e.g. PLCβ, γ and δ), insulin receptor substrates (IRS-1 and IRS-2), phosphoinositide 3-kinase (PI3 kinase) p110γ subunit, the guanine nucleotide release factor SOS, rasGAP, dynamin, CDC25, Tiam-1, Vav, guanine nucleotide exchange factors (e.g. GRP-1, ARNO, cytohesin) and β-spectrin. The sequences, ligands and relative binding affinities of a variety of PH domains are known in the art (see, for example, Bottomley et al., supra (1998)).

A preferred PH domain is a PH domain of a PLC, such as the PIP2-indicator PH domain of PLCδ1. The cloning and expression of the PH domain of PLCδ1, and its use in membrane molecule indicator polypeptides, is described in the Example, below.

An alternative PH domain of a PLC is the PH domain of PLCβ. PLCβ is responsible for physically cleaving PIP2, and thus the PH domain therefrom can be used to determine tranlocation or disassociation from the membrane of the actual PIP2 lipids cleaved by PLCβ. The PLCβ PH domain sequence is known in the art (e.g. Rebecchi et al., *Annu. Rev. Biophys. Biomol. Struct.* 27:503–528 (1998)).

In another embodiment, the phosphatidylinositol indicator domain is an FYVE domain. FYVE domains have been demonstrated to specifically bind to PtdIns (3)P. FYVE domains generally contain eight conserved cysteines, which coordinate two $Zn^{2+}$ ions in a cross-braced topology, a conserved R(R/K)HHCRXCG (SEQ ID NO:1) motif surrounding the third and fourth cysteine residues, and several highly conserved hydrophobic residues (see, for example, Stenmark et al., supra (1999), and Gaullier et al., *Chem. Phys. Lipids* 98:87–94 (1999)). FYVE domains have been found in mammalian, yeast and *C. elegans* proteins. Exemplary FYVE domain containing proteins include EEA1, Fab1p, YOTB, Vac1p, Vps27p, Hrs, Smad anchor for receptor activation (SARA), Fgd1, and have also been described in a large number of proteins of unknown function whose sequences are available in public databases (Stenmark et al., supra (1999)).

In another embodiment, the phospholipid indicator domain is a C2 domain. C2 domains are about 130 amino acids in length, and have been found in single or multiple copies in over 60 proteins. C2 domains bind a variety of ligands and substrates, including $Ca^{2+}$, phospholipids, inositol polyphosphates and intracellular proteins. C2 domains are found, for example, in synaptotagmin I–VIII, rabphilin, phosphatidylserine decarboxylase, protein kinase C, GAPs, perforin, PLC family members, BCR, ABR, PI3-kinase, cytosolic phospholipase A2, and have also been described in a large number of proteins of unknown function whose sequences are available in public databases (reviewed in Nalefski et al., *Protein Science* 5:2375–2390 (1996)).

In yet another embodiment, the phospholipid indicator domain is an SH2 domain. SH2 domains are well-characterized mediators of protein-protein interactions, but in addition certain SH2 domains bind phosphoinositides. For example, the SH2 domains from p85α and c-Src have been shown to directly and selectively bind PtdIns $(3, 4, 5)P_3$ (Bottomley et al., supra (1998)). The sequences of a variety of SH2 domains are known in the art.

In a further embodiment, the phospholipid indicator domain is a lipid binding domain of an actin binding protein, such as the lipid binding domain of the actin monomer sequestering protein profilin; the actin filament severing proteins gelsolin, villin, severin, adseverin, destrin and cofilin; the protein gCap39, which blocks the ends of actin filaments; and the actin filament cross-linking protein α-actinin (reviewed in Janmey, supra (1995)). The sequences of a variety of lipid binding domains of actin binding proteins are known in the art.

In another embodiment, the phospholipid indicator domain is a lipid binding domain of a clathrin adaptor protein, such as residues 5–80 of AP-2 (α-subunit), which specifically associates with PtdIns $(3, 4, 5)P_3$, or residues 1–304 of AP-3, which specifically associates with pyrophosphate $(PP)-InsP_5$ (reviewed in Bottomley et al., supra (1998)). The sequences of a variety of lipid binding domains of clathrin adaptor proteins are known in the art.

Other membrane molecule indicator domains can be readily identified, for example, by database searching and by structural predictions based on sequence or structural homology to known membrane molecule indicator domains, as described above.

Association between a MMID and a membrane molecule can be determined by binding assays known in the art. For example, association can be determined by co-immunoprecipitation assays, sedimentation assays, affinity chromatography, two-hybrid assays, gel-overlay assays, radiolabeled ligand binding assays, and the like. Association between molecules can also be determined by surface plasmon resonance (SPR) on BIAcore, nuclear magnetic resonance (NMR) spectroscopy, circular dichroism (CD) spectroscopy, and mass spectroscopy. Association between a MMID and lipid membrane molecule can conveniently be determined by adsorbing the MMID to a vesicle containing the lipid, and sedimenting the vesicle-bound protein by centrifugation. Such methods are reviewed, for example, in Winzor, *J. Mol. Recognit.* 13:279–298 (2000); and Bottomley et al., supra (1998).

The membrane molecule indicator domains described herein need not have the exact sequence of a domain found in a native sequence, so long as the domain retains the membrane molecule indicator function of the native sequence. Thus, a membrane molecule indicator domain can be a variant sequence having one or several amino acid additions, deletions or substitutions compared with a native amino acid sequence. Such modifications can be advantageous, for example, in enhancing the stability, expression level, or binding specificity of the domain, as well as for facilitating chimeric polypeptide construction. The function of a variant MMID can be confirmed by the binding assays described above.

Modifications to the amino acid sequence of a MMID can be randomly generated, such as by random insertions, deletions or substitutions of nucleotides in a native MMID nucleic acid molecule. Alternatively, modifications can be directed, such as by site-directed mutagenesis of a nucleic acid molecule encoding a native MMID.

The skilled person appreciates that extensive guidance in predicting which amino acid residues of a MMID can be modified, while retaining membrane molecule indicator ability, is provided by examining alignments between orthologs and other members of a particular MMID family. It is well known in the art that evolutionarily conserved amino acid residues and motifs are more likely to be important for maintaining biological activity than less well-conserved residues and domains. Thus, it would be expected that substituting a residue that is highly conserved among MMIDs within a family or across species with a non-conserved residue may be deleterious, whereas making the same substitution at a residue which varies widely would likely not have a significant effect on biological activity. These guiding principles have been confirmed for a variety of MMID containing proteins by mutagenesis studies. In general, a variant MMID will have at least 70% identity, more preferably at least 75% identity, including at least 80%, 85%, 90%, 95%, 98%, 99% or greater identity to the native domain to which the variant domain is most closely related.

Thus, as a non-limiting example, a PIP2 indicator domain can be a domain that has at least 70% identity, more preferably at least 75% identity, including at least 80%, 85%, 90%, 95%, 98% or greater identity to amino acids 1–174 of the human PLCδ-1 sequence (GenBank Accession No. NM_006225).

As used herein, the term "membrane anchoring domain" refers to the portion of a membrane molecule indicator polypeptide that localizes the polypeptide to a particular membrane. Membrane anchoring domains suitable for localizing polypeptides to membranes of interest are known in the art.

For example, a membrane anchoring domain suitable for localizing a polypeptide to the plasma membrane is the C-terminal sequence CaaX (where "a" is an aliphatic residue, and "X" is any residue, generally L). An exemplary membrane anchoring domain suitable for localizing a polypeptide to the endoplasmic reticulum is the C-terminal sequence KDEL (SEQ ID NO:2), assuming a signal sequence present at the N-terminus. Additionally, membrane anchoring domains can be small proteins, and portions of proteins, that confer appropriate localization to the membrane molecule indicator polypeptide when present in a chimera.

Optionally, the membrane anchoring domain can be a second membrane molecule indicator domain that associates with a different membrane molecule than the first membrane molecule indicator domain, and that is not co-regulated with the first membrane molecule. For example, in order to determine membrane abundance of PIP2, an appropriate indicator composition can include a membrane molecule indicator domain that associates with PIP2 (e.g. a PH domain) fused to a donor fluorescent domain, and a membrane molecule indicator domain that associates with a different membrane molecule that is not co-regulated with PIP2 fused to an acceptor domain, which thus serves to anchor the acceptor domain to the plasma membrane.

As used herein, the terms "donor fluorescent domain" and "acceptor fluorescent domain" refer to a pair of moieties selected so as to exhibit fluorescence resonance energy transfer (FRET) when the donor moiety is excited with appropriate electromagnetic radiation or becomes luminescent.

The donor fluorescent domain is excited by light of appropriate intensity within its excitation spectrum, and emits the absorbed energy as fluorescent light. When the acceptor fluorescent domain is positioned to quench the donor fluorescent domain in the excited state, the fluorescence energy is transferred to the acceptor fluorescent domain, which can emit fluorescent light. FRET can be manifested as a reduction in the intensity of the fluorescent signal emitted from the donor fluorescent domain, by reduction in the lifetime of the excited state of the donor fluorescent domain, or by emission of fluorescent light at the longer wavelengths (lower energies) characteristic of the acceptor fluorescent domain. When the association between the MMID and the corresponding membrane molecule changes, the donor and acceptor fluorescent domains physically separate (or come closer together), and FRET is decreased (or increased) accordingly (see FIG. 1).

One factor to be considered in choosing the fluorescent domain pair is the efficiency of fluorescence resonance energy transfer between them. Preferably, the efficiency of FRET between the donor and acceptor moieties is at least 10%, more preferably at least 50% and even more preferably at least 80%. The efficiency of FRET can easily be empirically tested using the methods described herein and known in the art.

The efficiency and detectability of FRET also depend on the separation distance and the orientation of the donor and acceptor fluorescent domains, as well as the choice of fluorescent domains. Considerations for the choice of fluorescent domains are well known in the art, and described, for example, in U.S. Pat. Nos. 5,998,204 and 5,981,200. For example, it is preferred that the emission spectrum of the donor fluorescent domain overlap as much as possible with the excitation spectrum of the acceptor fluorescent domain. In addition, the excitation spectra of the donor and acceptor fluorescent domains should overlap as little as possible so that a wavelength region can be found at which the donor fluorescent domain can be excited selectively and efficiently without directly exciting the acceptor moiety. Likewise, the emission spectra of the donor and acceptor fluorescent domains should have minimal overlap so that the two emissions can be distinguished. Furthermore, it is desirable that the quantum yield of the donor fluorescent domain, the extinction coefficient of the acceptor fluorescent domain, and the quantum yield of the acceptor fluorescent domain be as large as possible.

For example, in a suitable pair of fluorescent domains, the donor fluorescent domain is excited by ultraviolet light (<400 nm) and emits blue light (<500 nm), while the acceptor fluorescent domain is efficiently excited by blue light (but not by ultraviolet light) and emits green light (>500 nm). In an alternative pair of fluorescent domains, the donor fluorescent domain is excited by violet light (about 400–430 nm) and emits blue-green light (450–500 nm), while the acceptor fluorescent domain is efficiently excited by blue-green light (but not by violet light) and emits yellow-green light (about 520–530 nm).

Generally, the donor fluorescent domain and acceptor fluorescent domain will be fluorescent proteins, as described below. Alternatively, the donor can contain a tag, such as an artificial tetracysteine-based peptide tag, to which a cell permeable fluorescent label, such as FLASH-EDT$_2$, can bind (e.g. Griffin et al., *Science* 281:269–272 (1998)).

Fluorescent proteins suitable for use as donor or acceptor fluorescent domains in the compositions and methods of the invention have been isolated from a number of species, including jellyfish (e.g. Aequorea species) and coral (e.g. Renilla species and Discosoma species).

In one embodiment, the donor and/or acceptor fluorescent domain is a "green fluorescent protein" or "GFP," such as a native GFP from an Aequorea or Renilla species, an ortholog of a GFP from another genus, or a variant of a native GFP with optimized properties. As used herein, the term "GFP variant" is intended to refer to polypeptides with at least about 70%, more preferably at least 75% identity, including at least 80%, 90%, 95% or greater identity to a native GFP, such as Aequorea victoria GFP.

A variety of GFP variants having useful excitation and emission spectra, have been engineered by modifying the amino acid sequence of a naturally occurring Aequorea or Renilla GFP (see, for example, U.S. Pat. Nos. 5,625,048 and 5,998,204; Miyawaki et al., Nature 388:882–887 (1997); Delagrave et al., Biotechnology 13:151–154 (1995); Pollok et al., Trends in Cell Biol. 9:57–60 (1999)). Additionally, a variety of enhanced GFPs (or EGFPs) with optimized codons for expression in human cells, are known in the art (e.g. ECFP and EYFP).

GFP variants with optimized dimerization properties can also be prepared. It is postulated that the weak dimerization observed between GFPs (e.g. kD about 100 $\mu$M) allows donor and acceptor fluorescent domains present on separate polypeptide chains (e.g. FIG. 1B or 1D) to associate at the membrane and exhibit FRET, even at low expression levels where based simply on polypeptide concentration at the membrane, FRET would not be expected. The dimerization is suitably weak so that once dissociated from the membrane or from the membrane molecule, the donor and acceptor fluorescent domains separate so as to no longer exhibit FRET. GFP variants with altered dimerization properties can be selected so as to optimize the differential in FRET between alternatives configurations. For example, GFP variants with slightly higher, but still moderate, dimerization (e.g. kD about 25 $\mu$M) are expected to provide for suitably high FRET at the membrane even at low polypeptide expression levels, while still separating once dissociated from the membrane or from the membrane molecule.

Cyan fluorescent proteins (CFPs) are variant GFPs that contain the mutation Y66W with respect to Aequorea Victoria GFP. Yellow fluorescent proteins (YFPs) are variant GFPs that contain aromatic residues at position 203. Blue fluorescent proteins (BFPs) are variant GFPs that contain a Y66H mutation. A group of GFPs which lack the near-UV excitation peak, but retain the wild-type GFP emission peak, have Ser65 substitutions. Other variants of native GFPs with useful fluorescent properties are known in the art, or can be readily prepared by random or directed mutagenesis of a native GFP. Exemplary pairs of donor and acceptor fluorescent domains include BFP-GFP and CFP-YFP.

In another embodiment, the donor and/or acceptor fluorescent domain is a "DsRed," such as a native DsRed from a Discosoma species, an ortholog of DsRed from another genus, or a variant of a native DsRed with optimized properties (e.g. a K83M variant or DsRed2 (available from Clontech)). As used herein, the term "DsRed variant" is intended to refer to polypeptides with at least about 70%, more preferably at least 75% identity, including at least 80%, 90%, 95% or greater identity to a native DsRed, such as a Discosoma DsRed. Other variants of native DsReds with useful fluorescent properties are known in the art, or can be readily prepared by random or directed mutagenesis of a native DsRed (see, for example, Fradkov et al., FEBS Lett. 479:127–130 (2000)).

Other exemplary pairs of donor and acceptor fluorescent domains, respectively, include GFP-dsRED2 and YFP-dsRED2.

Included within the term "donor fluorescent domain" is a bioluminescent domain, such as luciferase from Renilla, related species, and variants thereof. Renilla luciferase emits blue light in the presence of an appropriate substrate, such as coelenterazin, which can be transferred to an appropriate fluorescent acceptor domain, such as a GFP, in a process called Bioluminescence Resonance Energy Transfer, or BRET. BRET is described, for example, in Angers et al., Proc. Natl. Acad. Sci. USA 97:3684–3689 (2000); Xu et al., Proc. Natl. Acad. Sci. USA 96:151–156 (1999); and components are commercially available from BioSignal Packard (Montreal, Canada). Those skilled in the art can readily apply the compositions and methods described herein with respect to FRET, to compositions and methods involving BRET.

In constructs in which the donor fluorescent domain and the acceptor fluorescent domain are present on the same polypeptide, the fluorescent domains can optionally be separated by a flexible "linker sequence." An appropriate linker sequence allows the donor and acceptor fluorescent domain to be functionally coupled when the single MMID (FIG. 1A), or pair of MMIDs (FIG. 1B), are associated with a membrane molecule, such that FRET is high, and functionally uncoupled when the MMIDs are not associated with the membrane molecule, such that FRET is low (FIGS. 1D and E). In order to optimize the FRET effect, the average distance between the donor and acceptor fluorescent domains should become less than about 10 nm when the MMID is associated with the membrane molecule (e.g. from 1 nm to 10 nm).

The linker moiety preferably is between about 1 and 50 amino acid residues in length, preferably between about 2 and 30 amino acid residues. A preferred linker moiety contains, or consists of, the sequence Gly-Gly, Ser-Gly or Gly-Ser. Linker moieties and their applications are well known in the art and described, for example, in U.S. Pat. Nos. 5,998,204 and 5,981,200, and Newton et al., Biochemistry 35:545–553 (1996).

The invention provides isolated nucleic acid molecules, which alone or in combination as components of a kit encode membrane molecule indicator polypeptides, including each of the exemplary indicators shown schematically in FIGS. 1, 9 and 10 and described above.

As used herein, the term "nucleic acid molecule" refers to a polynucleotide comprised of either DNA or RNA; which can be single- or double-stranded; which can optionally contain one or more non-natural nucleotides, such as nucleotides having modifications to the base, the sugar, or the phosphate portion; and which can optionally contain one or more non-natural linkages, such as phosphothioate linkages.

As used herein, the term "kit" refers to two or more component nucleic acid molecules packaged or sold for use together. The kit components will be contained either in a single container or separate containers. The kit can further optionally contain written instructions for use of the components in the methods of the invention, and/or buffers and components suitable for such methods.

The invention nucleic acid molecules are preferably operatively linked to a promoter of gene expression. As used herein, the term "operatively linked" is intended to mean that the nucleic acid molecule is positioned with respect to either the endogenous promoter, or a heterologous promoter, in such a manner that the promoter will direct the transcription of RNA using the nucleic acid molecule as a template.

Methods for operatively linking a nucleic acid to a heterologous promoter are well known in the art and include, for example, cloning the nucleic acid into a vector containing the desired promoter, or appending the promoter to a nucleic acid sequence using PCR. A nucleic acid molecule operatively linked to a promoter of RNA transcription can be used to express membrane molecule indicator transcripts and polypeptides in a desired host cell or in vitro transcription or transcription-translation system.

The choice of promoter to operatively link to an invention nucleic acid molecule will depend on the intended application, and can be determined by those skilled in the art. For example, if the encoded polypeptide may be detrimental to a particular host cell, it may be desirable to link the invention nucleic acid molecule to a regulated promoter, such that gene expression can be turned on or off. Alternatively, it may be preferred to have expression driven by either a weak or strong constitutive promoter. Exemplary promoters suitable for mammalian cell systems include, for example, the SV40 early promoter, the cytomegalovirus (CMV) promoter, the mouse mammary tumor virus (MMTV) steroid-inducible promoter, and the Moloney murine leukemia virus (MMLV) promoter. Promoters suitable in yeast include, for example, ADH promoter (*S. cerevisiae*) and the inducible Nmt promoter (*S. pombe*).

It will be appreciated that a nucleic acid molecule encoding a polypeptide containing a MMID and a donor fluorescent domain, and a nucleic acid molecule encoding a polypeptide containing a MMID and an acceptor fluorescent domain (e.g. FIGS. 1B and 1D) can optionally be present on the same vector or under the control of the same promoter. Such constructs are advantageous, for example, in simplifying introducing the nucleic acid molecules into a cell and in ensuring 1:1 stoichiometry of the donor and acceptor in the pair. Alternatively, the nucleotide sequences encoding the two polypeptides can be present on separate vectors or under the control of different promoters.

The invention further provides a vector containing an isolated nucleic acid molecule encoding a membrane molecule indicator polypeptide. Exemplary vectors include vectors derived from a virus, such as a bacteriophage, a baculovirus or a retrovirus, and vectors derived from bacteria or a combination of bacterial sequences and sequences from other organisms, such as a cosmid or a plasmid. The vectors of the invention will generally contain elements such as an origin of replication compatible with the intended host cells; one or more selectable markers compatible with the intended host cells; and one or more multiple cloning sites. The choice of particular elements to include in a vector will depend on factors such as the intended host cells; the insert size; whether regulated expression of the inserted sequence is desired; the desired copy number of the vector; the desired selection system, and the like. The factors involved in ensuring compatibility between a host cell and a vector for different applications are well known in the art.

For recombinant expression of the encoded polypeptide, the isolated nucleic acid molecules will generally be operatively linked to a promoter of gene expression, as described above, which may be present in the vector or in the inserted nucleic acid molecule.

Also provided are cells containing membrane molecule indicators, including each of the exemplary indicators shown schematically in FIGS. 1, 9 and 10 and described above, and cells containing nucleic acid molecules encoding such indicators. The cells of the invention can advantageously express the encoded polypeptide(s) and thus be used in screens for agonists, antagonists and inverse agonists of signaling pathways indicated by properties of the membrane molecule; to functionally clone modulatory components of the signal transduction pathway in which the membrane molecule is involved; and to determine or confirm the function of potential modulatory components of the signal transduction pathway in which the membrane molecule is involved. Such applications are described further below.

The isolated nucleic acid molecule(s) will generally be contained within an expression vector, but optionally can be expressible DNA or RNA not contained within a vector. The isolated nucleic acid molecule(s) can be maintained episomally, or incorporated into the host cell genome. The cells of the invention can be prepared by introducing the nucleic acid molecules of the invention by any suitable means, including, for example, transfection, transduction, electroporation and microinjection, as well as by transgenic technology.

The cells of the invention can be prepared from any organism, including, for example, bacteria (e.g. *E. coli*), insects (e.g. Drosophila), yeast (e.g. *S. cerevisiae, S. pombe,* or *Pichia pastoris*), nematodes (e.g. *C. elegans*), amphibians (e.g. Xenopus embryos and oocytes) and mammals (e.g. human, rodent or primate primary cells and established cell lines, such as COS, CHO, 3T3, N1E-115, HEK, etc., representing either a normal or diseased state of the mammal).

The cells of the invention can further recombinantly express, either stably or transiently, a known or candidate modulator of the membrane molecule, such as a known or candidate agonist, antagonist or reverse agonist peptide; a known or candidate receptor; or a known or candidate effector molecule.

As used herein, the term "recombinant expression," with respect to expression of a signaling polypeptide, refers to transient or stable expression of a polypeptide from a recombinant nucleic acid molecule. Recombinant expression is advantageous in providing a higher level of expression of the polypeptide than is found endogenously, and also allows expression in cells or systems in which the polypeptide is not normally found.

The term "recombinant nucleic acid molecule" is intended to refer to a nucleic acid molecule that has been constructed, at least in part, by molecular biological methods, such as PCR, restriction digestion or ligation. A recombinant nucleic acid expression construct generally will contain a constitutive or inducible promoter of RNA transcription appropriate for the host cell or transcription-translation system, operatively linked to a nucleotide sequence that encodes the polypeptide of interest. The expression construct can be DNA or RNA, and optionally can be contained in a vector, such as a plasmid or viral vector.

The construction of expression vectors and the expression of genes in transfected cells involves the use of molecular cloning techniques well known in the art and described, for example, in Sambrook et al., Molecular Cloning—A Laboratory Manual, Cold Spring Harbor Laboratory, Cold Spring Harbor, N.Y., (1989) and Current Protocols in Molecular Biology, F. M. Ausubel et al., eds., (Current Protocols, a joint venture between Greene Publishing Associates, Inc. and John Wiley & Sons, Inc., (most recent Supplement).

The nucleotide sequences of various receptors and effectors, and methods of recombinantly expressing the encoded polypeptides in a variety of cell types, are well known in the art.

The invention further provides membrane molecule indicator polypeptides. The invention polypeptides include polypeptides recombinantly expressed by the invention nucleic acid molecules, as well as constructs produced by chemically coupling some or all of the component domains, which themselves can be recombinantly produced. The expressed polypeptides can optionally be isolated from a transcription-translation system or cell, by biochemical and immunological purification methods known in the art. To facilitate isolation, the invention polypeptides can optionally be fused to a tag sequence, such as an epitope tag, a GST polypeptide or a 6×His fusion.

The invention polypeptides can optionally be introduced into a whole cell, such as by recombinant expression or microinjection, and the cells used in the methods described herein. The invention polypeptides can alternatively be introduced into a lipid bilayer, such as a cellular membrane extract, or an artificial lipid bilayer (e.g. a liposome vesicle). Methods of preparing lipid bilayers containing desired amounts and types of molecules, including the membrane molecules and MMID polypeptides described herein, are known in the art.

The invention also provides a method of determining a property of a membrane molecule. The method is practiced by
(a) providing a cell or lipid bilayer comprising a membrane molecule indicator; and
(b) determining FRET between the donor fluorescent domain and the acceptor fluorescent domain,
wherein FRET between the donor domain and the acceptor domain is indicative of a property of the membrane molecule.

Also provided is a method of identifying a compound that modulates a property of a membrane molecule. The method is practiced by
(a) contacting a cell or lipid bilayer comprising a membrane molecule indicator with one or more test compounds, wherein the cell or bilayer further comprises the membrane molecule; and
(b) determining FRET between the donor fluorescent domain and the acceptor fluorescent domain following contacting,
wherein increased or decreased FRET following contacting indicates that the test compound is a compound that modulates a property of the membrane molecule.

The lipid bilayer useful in such methods can be a whole cell, which naturally or recombinantly expresses the membrane molecule, or a cellular extract containing the plasma membrane or vesicular membranes. Alternatively, the lipid bilayer can be a lipid vesicle, which can include either natural or synthetic lipids or both, into which a membrane molecule of interest is incorporated. Lipid vesicles are advantageous in that the abundance of the membrane molecule (and, optionally, of other signaling molecules of interest) can be controlled.

The methods of the invention are useful in the practice of essentially any application for which a readout of signal transduction mediated through membrane molecules is useful. Such applications are well known in the art.

Exemplary applications include 1) identifying test compounds that act as agonists, antagonists, inverse agonists or natural ligands of receptors (described further below); 2) expression cloning of peptide agonists, antagonists and inverse agonists of receptors; 3) expression cloning of novel modulators that affect the abundance, localization, conformation or post-translational modification state of the membrane molecule of interest (e.g. enzymes, enzyme inhibitors, transcriptional regulators, and the like), which themselves can be used as therapeutic drug targets; 4) determining the function of variants of known or predicted modulators of membrane molecules (e.g. determining the effect of SNPs, disease-associated mutations and engineered variations in receptors, effectors and the like); 5) establishing dose-response curves of modulators of membrane molecules (e.g. for predicting effective dose of a therapeutic); and 6) determining alterations in membrane molecules and modulators that reflect disease state, which can be applied to the development of diagnostic methods. Methods of using the compositions and methods described herein for such applications, and other applications relating to signal transduction, will be readily apparent to the skilled person.

As an example, the methods of the invention can be used to identify test compounds that are agonists, antagonists, inverse agonists or natural ligands of receptors, including G-protein coupled receptors (described further below), tyrosine kinase receptors (e.g. PDGF, IGF, FGF and EGF receptors and the like) and integrins. In the methods of the invention, the basal level of FRET can be determined in an unstimulated lipid bilayer. The lipid bilayers can then be contacted with a test compound, and FRET compared with an unstimulated bilayer. FRET is advantageous over fluorescent visualization methods in that both increases and decreases, relative to the basal level, can be readily determined. Increased or decreased FRET relative to the basal level is a reflection of the activity of the test compound as an agonist, antagonist or inverse agonist of the signaling pathway linked to the membrane molecule.

As used herein, the term "agonist" refers to a molecule that selectively activates or increases signal transduction. An agonist can act by any mechanism, such as by binding a receptor at the normal ligand binding site, thereby mimicking the natural ligand and promoting receptor signaling. An agonist can also act, for example, by potentiating the binding ability of the natural ligand, or by favorably altering the conformation of the receptor. The compositions and methods of the invention can advantageously be used to identify agonists that acts through any agonistic mechanism.

As used herein, the term "antagonist" refers to a compound that selectively inhibits or decreases signal transduction. An important subset of antagonist compounds that can advantageously be identified by the methods described herein, are referred to as "inverse agonists." Inverse agonists are antagonists that selectively inhibit or decrease signal transduction below basal levels.

An antagonist can act by any antagonistic mechanism, such as by binding to a ligand or receptor, thereby inhibiting their interaction. An antagonist can also act by modifying or altering the native conformation of a receptor. The methods of the invention can advantageously be used to identify an antagonist that acts through any antagonistic mechanism.

For therapeutic applications, an agonist preferably has an $EC_{50}$, and an antagonist or inverse agonist preferably has an $IC_{50}$, of less than about $10^{-7}$ M, such as less than $10^{-8}$ M, and more preferably less than $10^{-9}$ M. However, depending on the stability, selectivity and toxicity of the compound, an agonist with a higher $EC_{50}$, or an antagonist with a higher $IC_{50}$, can also be useful therapeutically. $EC_{50}$ and $IC_{50}$ of such compounds can be established by dose-response curves using the methods described herein.

As used herein, the term "test compound" refers to any molecule that potentially acts as an agonist, antagonist, inverse agonist or natural ligand of a signaling pathway reported by the membrane molecule indicator compositions and methods of the invention. A test compound can be a naturally occurring macromolecule, such as a polypeptide, nucleic acid, carbohydrate, lipid, or any combination thereof. A test compound also can be a partially or completely synthetic derivative, analog or mimetic of such a macromolecule, or a small organic molecule prepared by combinatorial chemistry methods.

Methods for preparing large libraries of compounds, including simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., Curr. Opin. Chem. Biol. 2:422–428 (1998); Tietze et al., Curr. Biol., 2:363–371 (1998); Sofia, Mol. Divers. 3:75–94 (1998); Eichler et al., Med. Res. Rev. 15:481–496 (1995); and the like. Libraries containing large numbers of natural and synthetic compounds also can be obtained from commercial sources.

The number of different test compounds to assay in the methods of the invention will depend on the application of the method. For example, one or a small number of test compounds can be advantageous in manual screening procedures, or when it is desired to compare efficacy among several predicted ligands, agonists or antagonists. However, it is generally understood that the larger the number of test compounds, the greater the likelihood of identifying a compound having the desired activity in a screening assay. Additionally, large numbers of compounds can be processed in high-throughput automated screening assays. Therefore, "one or more test compounds" can be, for example, 2 or more, such as 5, 10, 15, 20, 50 or 100 or more different compounds, such as greater than about $10^3$, $10^5$ or $10^7$ different compounds.

A lipid bilayer can be contacted with a test compound by any mode, such as by extracellular administration, by intracellular uptake of the compound, or by recombinant expression of the compound (in methods involving an intact cell). The contacting with the test compound can optionally take place in the presence of a known agonist or antagonist of the signaling pathway of interest, and the effect of the compound on agonist or antagonist-mediated signaling can be assessed.

In cases in which the test compound is a peptide, the peptide can preferentially be targeted to the membrane location of the membrane molecule of interest, such as the extracellular or intracellular face of the plasma membrane, Golgi, ER or the like, using known methods. For example, test compounds that are peptides can be expressed on the extracellular membrane of a cell or the invention, or on a second cell, by phage display methods known in the art. Alternatively, test compounds that are peptides can be secreted from a cell of the invention, or from a second cell, by expressing the peptide with a secretory signal.

As an example, the methods of the invention can be used to screen for G-protein coupled receptor (GPCR) agonists, antagonists and inverse agonists, as well as to identify the natural ligands of orphan GPCRs.

GPCRs are seven-transmembrane-domain polypeptides that transduce G-protein coupled signals in response to ligands. The natural agonists of different GPCRs range from peptide and non-peptide neurotransmitters, hormones and growth factors, to lipids, nucleoside-sugars, amino acids, light and odorants. GPCRs are involved in a variety of critical biological functions, including cell proliferation, differentiation and apoptosis. GPCRs have proven to be important targets of pharmaceuticals that affect a variety of diseases, including neurological and psychiatric disorders, vascular diseases, endocrinological disorders, and cancer. It is estimated that over 50% of current drugs are targeted towards GPCRs, and represent about a quarter of the 100 top-selling drugs worldwide.

The natural ligands of different GPCRs include peptides, biogenic amines, glycoproteins, nucleotides, ions, lipids, amino acids, light and odorants. Structurally, GPCRs can be divided into three major subfamilies, each of which currently includes orphan receptors as well as receptors whose ligands are characterized (reviewed in Gether, Endocrine Reviews 21:90–113 (2000)). A database containing links to the nucleotide and amino acid sequences of numerous mammalian GPCRs, including orphan GPCRs, is available at http://www.darmstadt.gmd.de/~gpcrdb/.

As used herein, the term "G-protein" refers to a class of heterotrimeric GTP binding proteins, with subunits designated G$\alpha$, G$\beta$ and G$\gamma$, that couple to seven-transmembrane cell surface receptors to couple extracellular stimuli to intracellular messenger molecules. G-proteins are distinguished by their G$\alpha$ subunits. The more than 20 different G$\alpha$ subunits, encoded by 17 different genes, can be grouped into four major families: G$\alpha$s, G$\alpha$i, G$\alpha$q, and G$\alpha$12. Signaling through GPCRs that couple to G$\alpha$q-containing G proteins activates PLC enzymes to hydrolyze PIP2 in the plasma membrane to DAG and IP3.

The specificity of G$\alpha$ subunits for GPCRs is determined by the C-terminal five amino acids of the G$\alpha$. Thus, a variety of signal transduction pathways can be assayed to determine signaling through a GPCR, by co-expressing a chimeric G$\alpha$ containing the five C-terminal residues of a G$\alpha$ known or predicted to couple to the receptor of interest (such as G$\alpha$i, G$\alpha$s or the promiscuous G$\alpha$16), with the remainder of the protein corresponding to a G$\alpha$ coupled to the GPCR that signals through a membrane molecule of interest (see Conklin et al., Nature 363:274–276 (1993), and Komatsuzaki et al., FEBS Letters 406:165–170 (1995)).

For example, in instances in which the membrane molecule indicator polypeptides are designed to indicate abundance of PIP2, cells (or other lipid bilayers) can contain a GPCR of interest, and optionally a G$\alpha$q or G$\alpha$16 (or chimeric or variant G$\alpha$ which functions as a G$\alpha$q). The basal level of FRET between acceptor and donor fluorescent domains linked to a MMID (or two MMIDs) that associate with PIP2 can be determined. In response to agonist-induced signal transduction through the GPCR, PIP2 is hydrolyzed and FRET is decreased, as exemplified in the cells described in the Example, below. Likewise, antagonistic or inverse agonistic effects can be determined by an increase in agonist-induced, or basal, levels of FRET.

In the cells described in the Example, below, in which the MMID associates with PIP2 in the plasma membrane, FRET is high in unstimulated cells. In the presence of a test compound that activates PLC (e.g. bradykinin), FRET is significantly lower than in unstimulated cells, as PIP2 in the membrane is hydrolyzed, and the donor and acceptor fluorescent domains are no longer in close proximity. Thus, the compositions and methods described in the Example, below, can be used to identify and compare test compounds that stimulate the activation of PLC, that decrease the basal level of PLC activation, or that antagonize agonist-induced PLC activation.

PIP2 hydrolysis leads to the production of the second messengers DAG and IP3. IP3 mediates the release of $Ca^{2+}$ from intracellular stores. $Ca^{2+}$ release has been used as a signaling assay in variety of research, diagnostic and screening applications. The methods described herein, which detect PIP2 hydrolysis, can be used in most applications in which determination of $Ca^{2+}$ release has proven useful.

As disclosed herein, determining PIP2 hydrolysis has certain advantages over determining $Ca^{2+}$ release, in that PIP2 hydrolysis is more proximal to receptor activation, and is thus less dependent on intermediate signaling steps that may introduce variability. As shown herein, signals that yield similar $Ca^{2+}$ responses have different PLC activation kinetics, suggesting that PIP2 hydrolysis follows receptor activation more faithfully than $Ca^{2+}$ responses.

Optionally, PIP2 hydrolysis, as determined by the FRET methods described herein, and $Ca^{2+}$ release, as determined using $Ca^{2+}$ indicator dyes known in the art, can both be assayed. Because $Ca^{2+}$ release is downstream of PIP2 hydrolysis, $Ca^{2+}$ release can be assayed simultaneously with FRET to confirm that the observed FRET reflects PIP2 hydrolysis.

Methods of determining and quantitating FRET at the single cell level, or in cell populations, are well known in the art or can be determined by the skilled person. For example, FRET can be measured using dual emission fluorescence microscopy, as described in the Example, below. Alternatively, FRET can be measured using fluorescent microscopy imaging methodology, which allows for simultaneous recordings from multiple cells.

As a further example, FRET can be determined with fluorescent lifetime. Briefly, upon excitation with an ultrashort pulse of light (e.g. about 0.01 ns), fluorophores have a characteristic decay in emission that is single exponential, and may last 0.1–10 ns, dependent on the fluorophore and conditions. It has been shown that the presence of a FRET acceptor dramatically shortens the decay time of the donor, which can be detected either using direct monitoring of the decay time (time domain monitoring), or using sine-modulated light, in the frequency domain (see, for example, Verveer et al., *Biophys. J.*, 78:2127–37 (2000)).

For high-throughput screening applications, FRET can be measured using fluorescence activated cell sorting (FACS), such as with a HeCd laser or frequency-double diode laser. FACS is advantageous in permitting the analysis of around 50,000 cells per second, which is orders of magnitude faster than visual detection methods. FACS also allows the isolation of cells for further growth, manipulation and identification of nucleic acid molecules encoding compounds that modulate association between membrane molecules and the MMIDs of the invention compositions.

Therefore, the compositions and methods of the invention are amenable to high-throughput screening for potential therapeutics.

The following examples are intended to illustrate but not limit the present invention.

EXAMPLE I

Preparation and Use of Membrane Molecule Indicator Compositions

This example shows the preparation of two pairs of nucleic acid molecules of the invention. In the first pair, the first nucleic acid molecule encodes a polypeptide containing a membrane molecule indicator domain (PH domain) and a donor fluorescent domain (CFP), and the second nucleic acid molecule encodes a polypeptide containing a membrane molecule indicator domain (PH domain) and an acceptor fluorescent domain (YFP). In the second pair, the first nucleic acid molecule encodes a polypeptide containing a membrane molecule indicator domain (PH domain) and a donor fluorescent domain (CFP), and the second nucleic acid molecule encodes a polypeptide containing a membrane anchoring domain (CaaX) and an acceptor fluorescent domain (YFP).

This example also shows the use of the pairs of nucleic acid molecules to determine the abundance of a membrane molecule (PIP2), by determining FRET between the donor and acceptor fluorescent domains. High FRET results from high PIP2 abundance at the plasma membrane, which indicates the resting state of the cell; decreased FRET results from PIP2 hydrolysis, which indicates signaling through a G-protein coupled receptor linked to PLC activation.

Experimental Procedures

Materials 1-oleoyl LPA, histamine, bradykinin (BK), phenyl-arsine oxide and quercetin were from Sigma Chemical Co. (St. Louis, Mo.); neurokinin A, caged IP3 (cat.# 407135) and ionomycin were from Calbiochem-Novabiochem Corp. (La Jolla, Calif.); Myo-[$^3$H] inositol (60 Ci/mmol) was from Amersham-Pharmacia Biotech. Fura-red (K salt) was from Molecular Probes Inc. (Eugene, Oreg.). All other chemicals were of analytical grade.

Constructs

The pleckstrin homology-domain of human phospholipase C δ1 was obtained from the Superhiro-PLCδ1 PH construct (AA 1–174, obtained from T. Meyer) and cloned into the eukaryotic expression vector pECFP-C1 (Clontech, Calif.). Two primers (PLCδPH1; 5' CCTGC GGCCG CGGTA CCGAT ATCAG ATGTT GAGCT CCTTC AC 3' (SEQ ID NO:3) and PLCδPH2; 5' CCGAA TTCCC GGGTC TCAGC CATGG ACTCG GGCCG GGACT TC 3' (SEQ ID NO:4)) were designed to generate the PH-domain in frame behind the CFP followed by a stop codon. The PCR-product was cloned into the pECFP plasmid with the restriction sites EcoRI and EcoRV on EcoRI and SmaI, leading to pECFP-PH.

YFP was obtained from yellow Cameleon 2.0 (obtained from A. Miyawaki and R. Tsien) and subcloned into cloning vector PGEM3z (Promega), via SacI and EcoRI, and subsequently into pcDNA3 (Invitrogen) via BamHI and EcoRI. PCR on YFP- pcDNA-3 with primers T7 (Promega) and GFP3; 5' GGCTG AGACC CGGGA ATTCG GCTTG TACAG CTCGT CCATG 3' (SEQ ID NO:5) was done to remove the stop codon. The PH domain PCR-product, taken between primers PLCδPH1 and PLCδPH2, was cloned in frame behind YFP with EcoRI and NotI, leading to pcDNA3YFPPH. To obtain pcDNA3eGFPPH, YFP was swapped with EGFP, using primers T7 and GFP3 on pcDNA3eGFP and restriction enzymes BamHI and EcoRI.

For YFP-CAAX and GFP-CAAX, the membrane localization sequence of K-Ras (KMSKD GKKKK KKSKT KCVIM; SEQ ID NO:6) was obtained by PCR from Bp180-CAAX (GenBank accession number M54968 and M38506), using primers CAAX3 5' CCGAA TTCCC GGGTC AAGAT GAGCA AAGAT GGTAA AAAG 3' (SEQ ID NO:7), containing an EcoRI site, and CAAX2; 5' CCTGC GGCCG CGGTA CCGAG ATCTT TACAT AATTA CACAC TT 3' (SEQ ID NO:8), that contained a NotI-site behind the stop codon. The final constructs were made by exchanging the PH domain from YFP-PH and GFP-PH for the CAAX domain using EcoRI and NotI. All clones were verified by sequence analysis. YFP-CAAX contained a point mutation (V instead of G in the CAAX domain), but this did not influence the membrane localization.

Constitutively active mutants of $G\alpha_q$ and $G\alpha_{12}$ subunits in pcDNA3 vectors were obtained from Dr. O. Kranenburg (Kranenburg et al., *Mol. Biol. Cell* 10:1851–1857 (1999)).

Cell Culture and Transfections

N1E-115 neuroblastoma cells were seeded in 6-well plates at about 25,000 cells per well on 25 mm glass coverslips, and cultured in 3 ml Dulbecco's Modified Eagle's medium (DMEM) supplemented with 10% FCS and antibiotics. Unless otherwise indicated, constructs were transfected for 6–12 hours using calcium phosphate precipitate, at 0.8 µg DNA/well. Following transfection, cells were incubated in serum- free DMEM for 12–48 hours. For fluorescence detections, coverslips with cells were transferred to a culture chamber and mounted on an inverted microscope. All experiments were performed in bicarbonate-buffered saline (containing, in mM, 140 NaCl, 5 KCl, 1 $MgCl_2$, 1 $CaCl_2$, 10 glucose, with 10 mM HEPES added), pH 7.2, kept under 5% $CO_2$, at 37° C.

Inositol Phosphate Determinations

Preparation, culture and labeling of bovine adrenal glomerulosa cells have been described in Balla et al., *J. Biol. Chem.* 269:16101–16107 (1994). Cells labeled with myo-[$^3$H] inositol for 24–48 hrs were stimulated by angiotensin II (30 nM) for the indicated times in a medium containing either $Sr^{2+}$ or $Ca^{2+}$. Reactions were terminated with perchloric acid and inositol phosphates were separated by HPLC essentially as described in Balla et al., supra (1994).

Confocal Microscopy and Image Analysis

For confocal imaging, a Leica DM-IRBE inverted microscope fitted with TCS-SP scanhead was used. Excitation of EGFP was with the 488 nm Argon ion laserline, and emission was collected at 500–565 nm. For translocation studies, a series of confocal images were taken at 2–10 second intervals and stored on disk. Determination of the ratio of membrane to cytosolic fluorescence by directly assigning regions of interest (ROIs) for membrane and cytosol was hampered by the shape changes of cells during experiments. Using Qwin software (Leica) this ratio was therefore calculated by post-acquisition automated ROI assignment and analysis. In brief, a binary mask of the transfected cell was lined out using a thresholding step on a smoothed image. From this mask, the area corresponding to the membrane was eroded by a selectable amount to delineate the membrane. Further erosion was then applied to reliably separate membrane from cytosol area, and the remaining area was taken to represent cytosol. This mask was updated for each image in a series, and translocation was expressed as ratio of the fluorescence values for membrane and cytosol area, to correct for bleaching. This approach corrects fully for cell movements and shape changes, and was able to reliably detect very minor translocations (using e.g. diluted agonists).

Fluorescence Determinations

For FRET experiments, cells were transferred to an inverted Zeiss Axiovert 135 microscope equipped with dry Achroplan 63× (NA 0.75) objective. Excitation of CFP was at 425±5 nm, and emission was collected with a 460 nm dichroic mirror. Emission of CFP and YFP was split using an additional 505 dichroic and filtered with 475DF30 and 540DF40 bandpass filters, respectively. Detection was with PTI model 612 analog photomultipliers, and for data acquisition, the FELIX software (PTI Inc.) was used. FRET was expressed as the ratio of CFP to YFP signals, the value of which was set as 1.0 at the onset of the experiment. Changes are expressed as percent deviation from this initial value of 1.0. For detection of intracellular $Ca^{2+}$, Yellow Cameleon 2.1 was used at the same wavelengths (Miyawaki et al., *Nature* 388: 882–887 (1997)).

For sustained stimulation, agonists and inhibitors were added to the medium from concentrated stocks. Stimulation with short pulses of NKA was performed by placing a glass micropipette (tip diameter about 2 µm) at about 25 µm from the cell using an Eppendorf microinjection system and applying pulses of pressure for 10 seconds. It was verified using Lucifer Yellow in the pipette that following termination of the pressure pulse the concentration at the cell rapidly dropped towards zero.

Loading and Flash Photolysis of Caged IP3

Before electroporation, adherent cells grown on coverslips were washed twice in intracellular buffer (containing in mM: 70 KCl, 70 Kglutamate, 2 $MgCl_2$, 0 $CaCl_2$, 5 phosphate buffer, pH 7.1) and then 70 µl of this intracellular buffer was added to the cells with 20 µM of Fura-red tetrapotassium salt and either 1, 10 or 100 µM of caged IP3. Electroporation was achieved by a series of 15 high-frequency square wave pulses, (1-second spaced, amplitude 150V, frequency 80 kHz, lasting 0.5 ms each) using 2 platina electrodes of 8×3 mm with 2.5 mm spacing. The efficiency of this method was assessed by control permeabilizations that were performed on the stage of a confocal microscope. This protocol caused complete permeabilization (based on equilibration of intracellular calcein concentrations with the extracellular buffer) of the cells in the area between the electrodes.

For photorelease of caged IP3, a single cell was illuminated with a short pulse of UV light (340–410 nm) from a 100 W HBO lamp using a shutter. The shutter open time was adjusted to give full release of caged IP3, that is no response being observed with a subsequent illumination. For partial photolysis, the flash intensity was adjusted by using neutral density filters placed in the illumination pathway.

Quantitation of Expression Levels

For quantitation of expression levels of CFP-PH and YFP-PH, cellular fluorescence was compared to the fluorescence of a solution of known concentration of purified, bacterially expressed CFP-PH or YFP-PH, following the method of Miyawaki et al., "Calcium signaling: a practical approach," Oxford University Press (in press). In short, CFP-PH and YFP-PH were expressed as GST-fusion proteins, and purified on glutathione sepharose beads. Protein concentration was measured by the BCA* Protein Assay (Pierce, Ill., USA). The solution (4.8 µM) was then introduced in a linear wedge-shaped chamber (0–170 µM thickness) that was placed on the microscope (using NA 0.7 objective), and the position of the chamber was adjusted to give a fluorescence readout that matched that of a single, CFP or YFP expressing cell. The estimate of the fluorescent protein concentration in the cell was obtained by comparing the local thickness of the wedge to that of an average cell (17 µM). Relative amounts of CFP-PH and YFP-PH expression in cells were always determined under conditions of full cytosolic localization of the constructs.

At the onset of each experiment, photomultiplier gains (high voltage) were adjusted to give a standard 6V output for the resting cell. Noting that over an extended range of light input, every 2-fold change in intensity corresponds to a 35V change in cathode voltage, cell intensities were measured. By comparing these to the values obtained with the GFPwedge, estimates of expression levels were obtained.

Fluorescence Recovery After Photobleaching (FRAP)

For FRAP experiments, cells were imaged using a Leica TCS-SP confocal microscope equipped with 63× (NA 1.3) oil immersion objective. The beam from an external ArKr laser (25 mW) was coupled into the backfocal plane of the objective via the epifluorescence excitation port, using a 30/70 beamsplitter, thus allowing simultaneous imaging and spot bleaching. Spots of about 1.3 μm (full width half maximum) were bleached (>95%) in the basal membrane using a single 30 ms pulse from the ArKr laser during data collection in linescan mode at 1000, 500 or 125 Hz. Data were corrected for slight (<7%) background bleaching and fitted with single exponents using Clampfit software (Axon Instruments, Calif.).

Results

Figure 2:
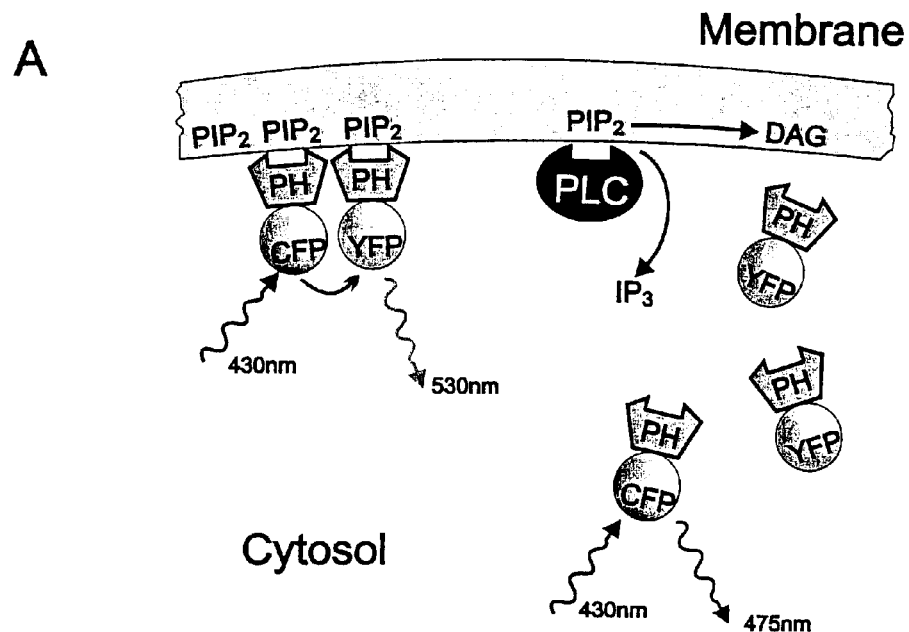
FIG. 2 shows fluorescence resonance detection of PH domain translocation. (A) Schematic representation of FRET occurring between CFP-PH and YFP-PH bound to the membrane. Upon hydrolysis of PI (4, 5)P2, PH domains translocate to the cytosol and FRET ceases. (B) Emission signals of CFP and YFP, collected at 475 and 530 nm respectively, and the ratio of 530/475, recorded from a single N1E-115 cell stimulated with bradykinin (BK, 1 $\mu$M). Signals were low-pass filtered at 2 Hz and sampled at 3 Hz. Scale bar for ratio signal shows percent deviation from baseline. (C) Confocal detection of GFP-PH translocation, depicted on the same scale. Images were collected once per 10 seconds, and the ratio of fluorescence intensities in membrane and cytosol (PM/Cyt) was deduced for each image by post-acquisition automated image analysis.
Figure 2:
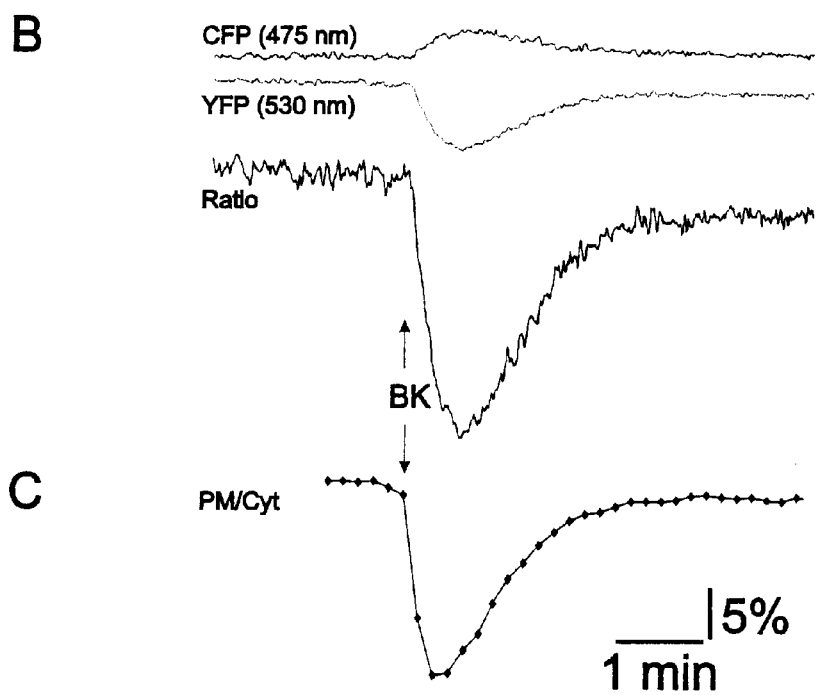

Fluorescence Resonance Energy Transfer Between Plasma Membrane-localized PLCδ1PH-CFP and PLCδ1PH-YFP PH-CFP and PH-YFP chimera were transiently transfected into N1E- 115 mouse neuroblastoma cells at a 1:1 molar ratio. After 1–2 days, cells were transferred to an inverted epifluorescence microscope and assayed for FRET by simultaneously monitoring the emission of CFP (475±15 nm) and of YFP (530±20 nm), while exciting CFP at 425±5 nm. In resting cells, PH-CFP and PH-YFP reside at the plasma membrane bound to PI (4, 5)P2, and the two fluorophores remain within resonance distance. Upon activation of PLC by the addition of bradykinin (BK), PI (4, 5)P2 is rapidly hydrolyzed and consequently PH domains can no longer bind to the plasma membrane. Depending on cell type (surface to volume ratio), it is estimated that the distance(s) between fluorophores increase about 200–1000 fold), and therefore FRET does not occur (FIG. 2). As a result, the donor (CFP) emission intensity increases, while the acceptor (YFP) emission decreases. By taking the ratio of CFP to YFP emission, the FRET signal becomes essentially independent on excitation intensity fluctuations and photobleaching.

The kinetics of BK-induced PLC activation in N1E-115 cells as detected by FRET is characterized by a rapid onset, with translocation peaking at 20–30 s after addition of the agonist. The decaying phase is somewhat slower, usually returning to baseline within 1 to 4 minutes. This time course is very similar to that deduced from confocal detection of PLCδ1PH-GFP translocation recorded under identical conditions (FIG. 2C). In this latter case, the data were extracted from a time series using post-acquisition automated image analysis (see Experimental Procedures). Similar translocation responses can be obtained by FRET in other cell types, including A431 epidermoid carcinoma cells, HEK293 embryonal kidney cells, and COS monkey kidney cells stimulated with a variety of ligands to Gq-coupled receptors.

The above described kinetics with a fast and rather complete translocation induced by BK, suggest that PIP2 depletion after stimulation is quite extensive. While most reports of agonist-induced PIP2 hydrolysis, as detected biochemically from [$^3$H]-inositol-labeled cells, show slower and less pronounced decreases in phosphoinositide levels, considerable agonist- and cell type-dependent variations exist, e.g. (Tilly et al., Biochem. J. 252:857–863(1988); van der Bend et al., Biochem. J. 285 (Pt I):235–240 (1992); Zhang et al., Mol. Pharmacol. 50:864–869 (1996)). Where early time points were also studied, rapid decreases in PIP2 levels have been detected (Wijelath et al., Biochem. Biophys. Res. Commun. 152:392–397 (1988); Divecha et al., EMBO J. 10:3207–3214 (1991); Stephens et al., Biochem. J. 296 (Pt 2):481–488 (1993)). For example, significant bradykinin-induced PIP2 decreases were reported to occur within 10 seconds in bovine aortic endothelial cells (Myers et al., Cell Signal. 1:335–343 (1989)), and at 1 minute in bombesin-stimulated 3T3 cells (Divecha et al., supra (1991)). Rapid recovery towards basal levels has also been found. Wijelath et al. reported as much as 85% hydrolysis of PIP2 at 5 seconds after stimulation of macrophages with interleukin, while PIP2 levels had recovered to 50% at 60 seconds (Wijelath et al., supra (1988)). Similar fast recovery was also seen in other cell types (Divecha et al., supra (1991); Stephens et al., supra (1993)). Since biochemical analyses have to rely upon measurements on cell populations, where not all cells give synchronized and identical responses (and many cells may not respond at all), it is not surprising to find differences between the results of measurements with these two alternative approaches.

Characterization of Fluorescence Signals

During agonist-induced translocation, several factors may affect the fluorescent properties of these PH domain chimeras as well as the transfer of fluorescent energy between them (Tsien, Annu. Rev. Biochem. 61:509–544 (1998)). For example, the move away from a compartment adjacent to the lipophilic membrane could alter fluorescent characteristics, and is also likely to alter FRET by increasing the degree of rotational freedom. While the relative influence of increased rotational freedom on the translocation-induced decrease in FRET is difficult to assess in this model sytem, fluorescence changes were analyzed in some further detail.

Figure 3:
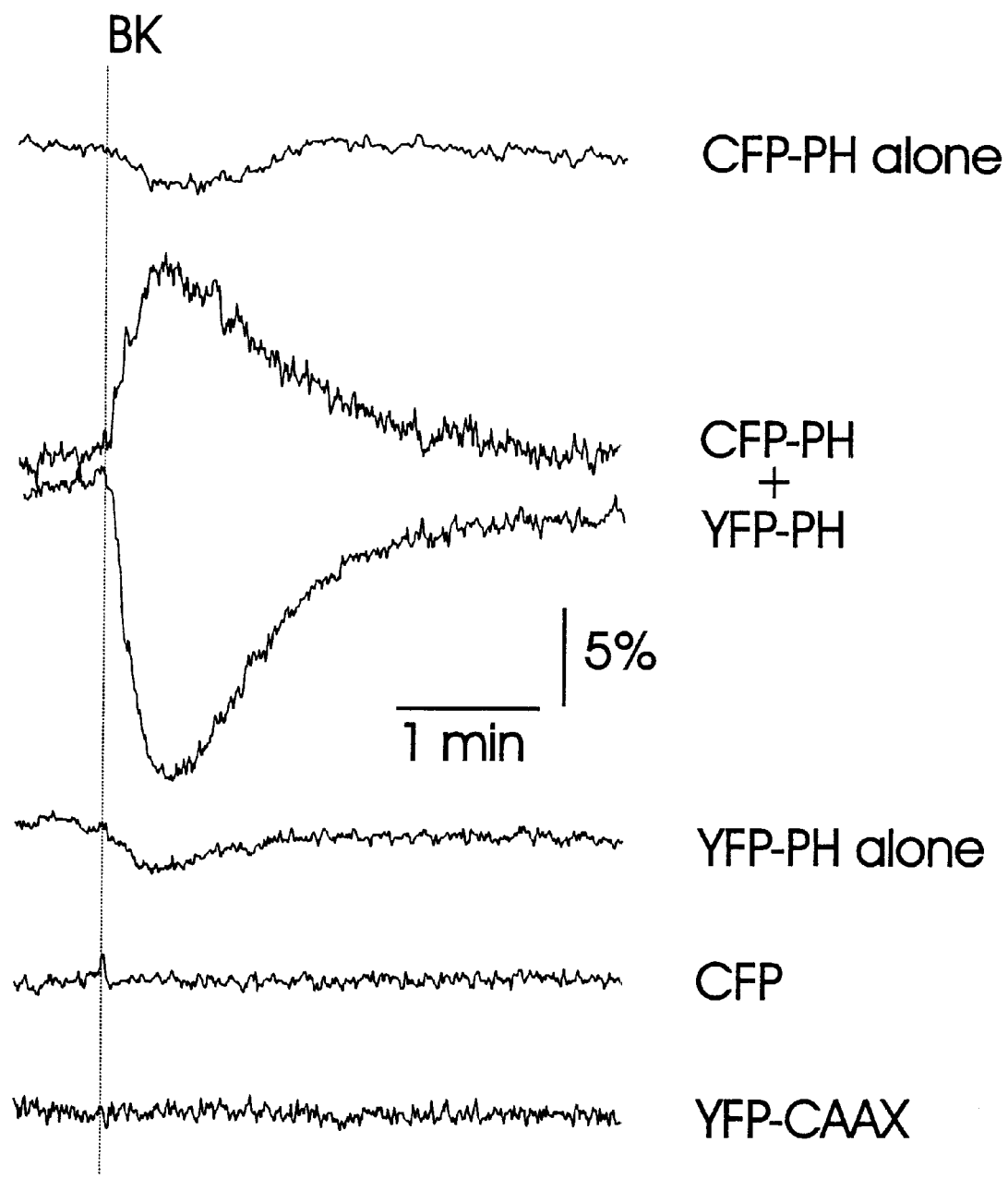
FIG. 3 shows characterization of fluorescence emission. Cells expressing constructs as indicated were stimulated with 1 μM bradykinin and fluorescence emission was detected at the indicated wavelength.

Cells were transfected with only one of the PLCδ1PH-CFP or PLCδ1PH-YFP constructs. After stimulation, a small but consistent transient fluorescence decrease was observed with either the CFP or the YFP-tagged PH domains (FIG. 3). The original green construct (PLCδ1PH-GFP) displayed similar behavior (not shown). This transient decrease is likely caused by fluoriphore displacement from the membrane, since it is not observed in cells that express a more stably membrane-anchored GFP-CAAX, nor is it seen in cells that express a mutated PLCδ1PH-GFP (R40L) (Varnai et al., J. Cell Biol. 143:501–510 (1998)) that can not bind PI(4, 5)P2 and, therefore, is cytosolic throughout the experiment. The precise mechanism that causes this decrease of emission upon cytosolic translocation is unknown; however, influence of the local microenvironment (e.g. hydrophobicity, charged groups, changing ion concentrations etc.) on the spectral properties of GFP seems likely (Tsien, supra (1998)). The "displacement" effect may explain why the translocation-induced decrease in YFP signal usually is somewhat larger than the increase in CFP fluorescence. However, expressing FRET as an emission ratio largely eliminates this effect.

FRET could also be measured in cells that coexpress PLCδ1PH-CFP with YFP-CAAX (not shown); however, using this pair, ratioing did not cancel the above mentioned displacement effect.

To assess the effects of construct concentrations on FRET, cells expressing various levels of the chimeric proteins were compared. Intracellular fluorescent protein concentrations were estimated by comparing the emission intensities of individual cells to those of a solution of bacterially expressed, purified protein of known concentration (Miyawaki et al., supra (in press); see Experimental Procedures). Based on these estimates, resonance could be observed in cells with expression levels between about 2–200 μM, over a 100-fold concentration range. However, FRET was not observed in cells expressing less than about 1 μM of each of the constructs. Very high expression levels, on the other hand, appeared to be detrimental to the cells (as judged from the appearance of membrane blebs and detachment of cells 2–3 days after transfection). Such cells were excluded from analysis. These data also revealed that PLCδ1PH-CFP expression levels (detected in fully translocated cells) did not differ more than about 2-fold from those of PLCδ1PH-YFP in most cells.

It was of interest to determine whether estimates of CFP and YFP concentrations can be used to calculate lipid concentrations and molecular proximity in the cells studied. Assuming a typical attached N1E-115 cell to be a pyramid having a 20×20 μm base and 10 μm height (having 1.3 pl volume and 1100 μm$^2$ surface), and assuming that (I) the concentration of both chimera is 20 μM; (II) 50% of fluorophores are located at the membrane (complete translocation roughly doubles the fluorescence in the cytosol); (III) the distribution of fluorophores is homogenous along the membrane; and (IV) fluorophores are insensitive to the local environment, then the calculated mean distance between fluorophores is 7–8 nm, which is close to the reported Forster radius (50 Angstrom) for FRET between this pair of fluorophores (Tsien, supra (1998)). However, it should be emphasized that these assumptions are valid only as first approximations. For example, we and others (Tall et al., Curr. Biol. 10:743–746 (2000)) noted that GFP-PH is not homogeneously localized along the plasma membrane. Also, as discussed above, the spectral properties of the fluorescent proteins are sensitive to the microenvironment. Nevertheless, these data set a lower limit for the density of PIP2 molecules available for PH binding at the inner surface of the plasma membrane.

GFP-PH Rapidly Shuttles Between Membrane and Cytosol

Figure 4:
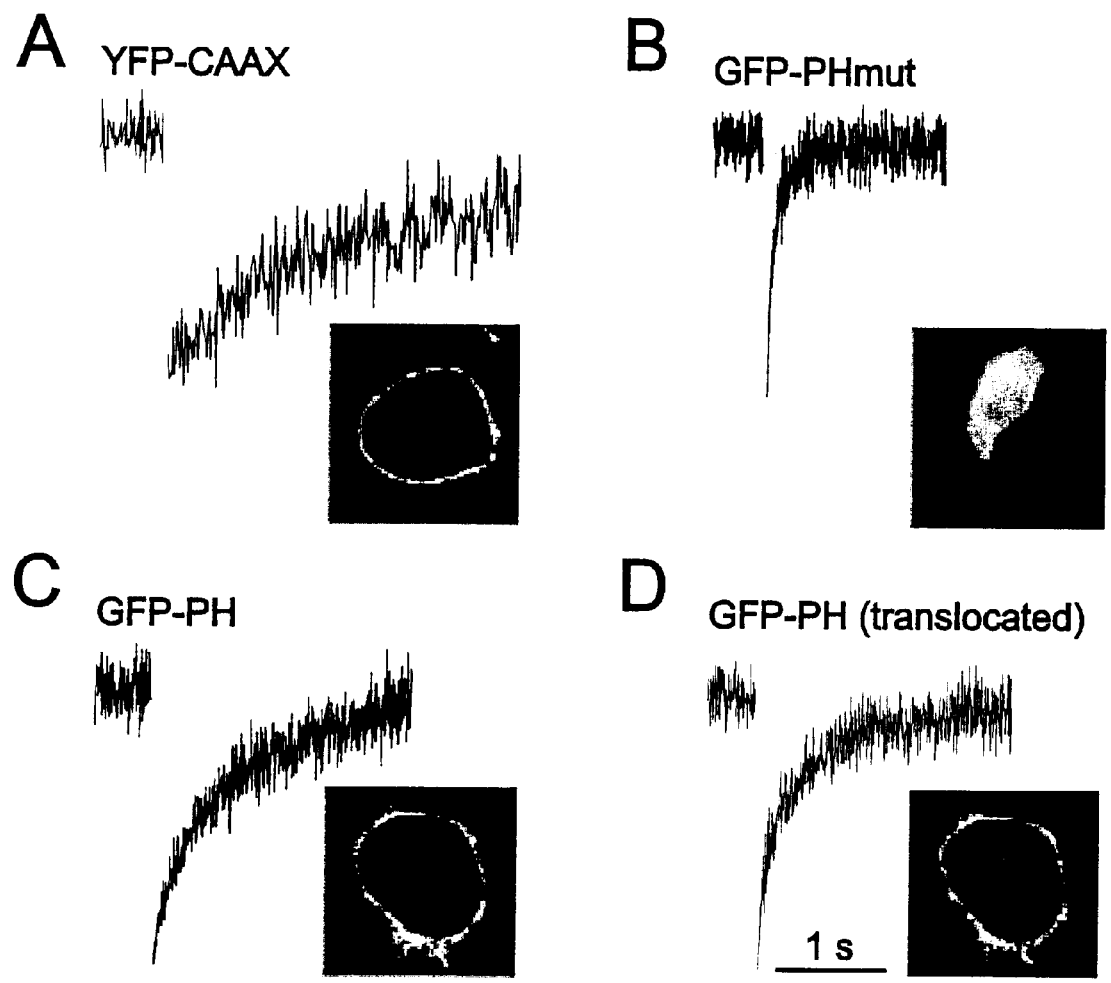
FIG. 4 shows Fluorescence Recovery After Photobleaching (FRAP) to reveal dynamic movements of GFP-PH between cytosol and membrane. Spots (approx. 1.3 μm full-width half maximum) were completely bleached in the basal membrane (or in the cytosol for B) with a 30 m-s pulse of 488 nm laser light, and recovery was monitored in line-scan mode in a confocal microscope. (A) FRAP of membrane-delimited YFP-CAAX; (B) cytosolic PLCδ1PH (R40L)-GFP mutant that cannot bind PI (4, 5)P2; (C) PLCδ1PH-GFP in a resting cell; (D) PLCδ1PH-GFP in a cell that has agonist-induced partial translocation of fluorescence. Insets show confocal images for the distribution of these constructs, taken from distinct cells.

Another important characteristic to address was membrane association and dissociation rates of the PH chimera. These rates directly influence reliability of FRET in reporting rapid changes in PLC activity, and are also relevant to the ability of PLC to hydrolyze PI(4, 5)P2 in cells that express high levels of the PLCδ1PH-GFP protein. Accordingly, fluorescence recovery after photobleaching (FRAP) experiments were performed to estimate the binding and dissociation kinetics of PLCδ1PH-GFP in the membrane. FIG. 4 shows representative results from such FRAP experiments in N1E-115 cells. In panels A and B, the recovery rates are depicted for GFP-CAAX and PLCδ1PH (R40L)-GFP, constructs that are delimited to the plasma membrane and the cytosol, respectively. The former presents the extreme of slow, purely membrane-delimited diffusion (2.81±0.31 s, n=15), and the latter of fast cytosolic diffusion (0.201±0.022 s, n=15). Since FRAP of membrane-localized PLCδ1PH-GFP is significantly faster than that of the membrane-delimited GFP-CAAX (1.22±0.23 s, n=40; p<0.0005; compare panel A and C), its recovery has to be partially through the cytoplasm. Thus, PI(4, 5)P2-PH binding is a dynamic process, with on-off rates in the order of seconds. In support of this notion, FRAP times further decreased during agonist-induced partial translocation, when association rates are increased due to the raised cytosolic GFP-PH levels (panel D). The rapid shuttling between membrane and cytosol of individual PLCδ1PH-GFP molecules could explain why PI(4, 5)P2 is still available for PLC-mediated hydrolysis or for binding of other proteins in cells expressing these chimeras.

Widefield FRET Detection Allows Prolonged Monitoring Independent of Cell Shape Changes.

Figure 5:
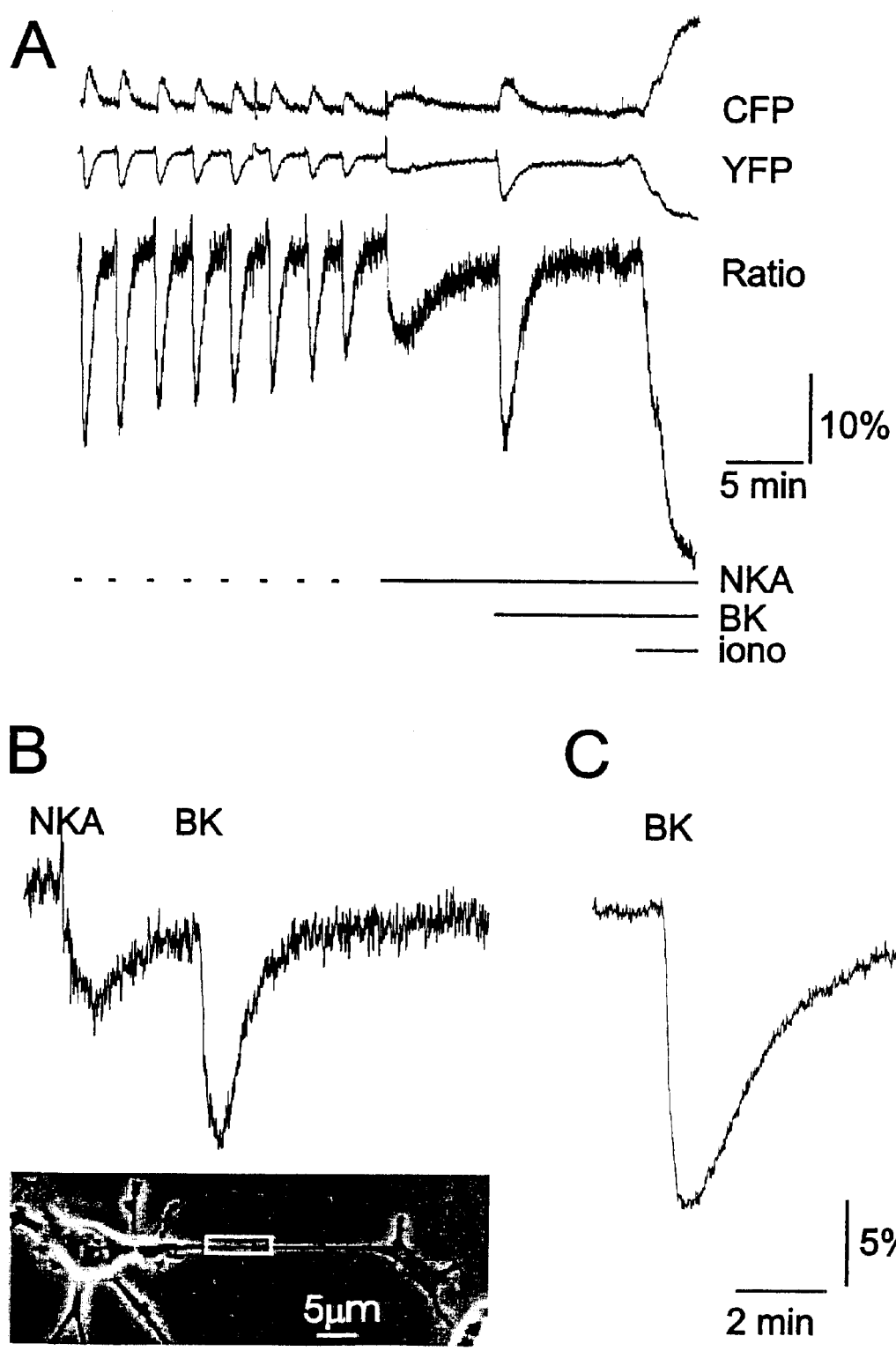
FIG. 5 shows PLC activation in single cells, neurites or in cell populations recorded by FRET. (A) A single N1E-115 cell was stimulated repeatedly with neurokinin A (NKA) as indicated by the lines (dashes, 10 s pulses of 100 μM NKA from a puffer pipette; solid line, addition of 1 μM final concentration to the culture dish). The response shows repeated PLC activation and partial desensitization. PLC activation induced by subsequently added bradykinin (BK, 1 μM) was not desensitized by NKA pretreatment. For calibration, maximal translocation was induced by adding 5 μM ionomycin+2 mM additional $Ca^{2+}$. (B) PLC activation in a single neurite of a neuroblastoma cell, differentiated by culturing in serum-free medium for 48 hours. Area of measurement (2.5×9 μm) is indicated in the micrograph. Excitation bandwidth was increased to 20 nm. (C) FRET recording from a cluster of about 15 transfected cells demonstrates improved signal-to-noise ratio and averaged kinetics (note the same scale for B and C).

Rapid confocal scanning of cells transfected with PLCδ1PH-GFP leads to considerable photobleaching (within 100 frames) and often causes severe phototoxic damage, manifested as membrane blebbing and loss of membrane integrity within minutes. Using wide-field optical detection and integrating emission from an entire cell (or even clusters of cells) allowed excitation intensity to be dimmed by as much as 100 to >1000 fold, while still retaining acceptable signal-to-noise ratio. Thus, FRET can be followed in single cells for extended periods of time without detectable cell damage. This permits recording of complex stimulation protocols, as shown in FIG. 5A. As shown therein, a single N1E-115 cell that is repeatedly stimulated with short pulses of neurokinin A (NKA) from a puffer pipette showed repeated PLC activation. The response to NKA displays incremental partial homologous desensitization of PLC activation, while the response to subsequently added BK is unaltered. Optimizing for low excitation intensity, recordings of several hours can be obtained with sub-second resolution.

In N1E-115 and other cells, addition of certain agonists causes rapid and significant shape changes. For instance, LPA causes neurites to retract and the cell soma to round up within 60 seconds (Jalink et al., Cell Growth Differ. 4:247–255 (1993)). In contrast, addition of BK has opposite effects, promoting a differentiated phenotype (van Leeuwen et al., Nat. Cell Biol. 1:242–248 (1999)). During confocal imaging, such shape changes (as well as the slight drift in focal plane that inevitably occurs over prolonged times) seriously complicate the quantification of GFP-PH translocation. Since FRET analysis uses the total integrated emission from a cell, shape changes and focal drift do not present problems.

In very flat and small cell structures such as neurites and lamellipodia (below approximately 2 μm in thickness), confocal imaging cannot detect translocation due to its inherent limit in z-axis resolution. However, in such cases changes in FRET can still be reliably detected as shown by the agonist-induced PLC activation recorded over a single neurite (FIG. 5B). FRET can also be recorded from cell populations (FIG. 5C) providing with an average response that would need analysis of hundreds of single cell recordings. Thus, detecting resonance between fluorescent protein-labeled PH domains overcomes a number of the limitations that are associated with confocal detection.

Determination of whether FRET Reports Changes in Membrane PI(4, 5)P2 or increases in cytosolic IP3

While PLCδ1PH-GFP has been introduced as an indicator of membrane PI(4, 5)P2 (Stauffer et al., Curr. Biol. 8:343–346 (1998); Varnai et al., supra (1998)), it also displays high affinity to IP3 (Hirose et al., Science 284:1527–1530 (1999)) which may exceed its affinity to PI(4, 5)P2, although it is difficult to accurately measure the latter as it is displayed in vivo. Based on such relative affinity estimates, Hirose and coworkers recently suggested that PLCδ1PH-GFP actually monitors IP3 increases rather than the changes in lipid levels in MDCK cells (Hirose et al., supra (1999)). They reported that microinjection of IP3 in MDCK cells was sufficient to cause displacement of PLCδ1PH-GFP from the membrane to the cytosol through competition for binding of the fluorescent construct to membrane PI(4, 5)P2. They also showed that expression of an IP3-5-phosphatase completely blocked the agonist-induced translocation of the fluorescent protein, and concluded that PI(4, 5)P2 changes do not make a significant contribution to the translocation response during stimulation.

While FRET analysis effectively monitors the result of PLC activation regardless of whether it is the lipid decrease or the IP3 increase that is more important for the translocation response, this question deserved a more detailed analysis. First it was determined whether intracellular applications of IP3 that generate a $Ca^{2+}$ signal comparable to that evoked by an agonist would cause translocation of the PLCδ1PH that is similar to what is caused by agonist stimulation. N1E-115 cells were loaded with 20 pM of the calcium indicator Fura red and 100 pM caged IP3 by in situ high frequency electroporation. Unlike microinjection, this technique allows setting of the final concentration of caged IP3 in the cytosol with high precision (see Experimental Procedures), as confirmed by the observation that upon electroporation, intracellular and extracellular fluorescence levels were equal. As shown in FIG. 6A, UV flash photolysis of 1 PM of caged IP3 rapidly mobilized $Ca^{2+}$ from internal stores, with no visible translocation of PLCδ1PH-GFP to the cytosol. Subsequent release of 10 $\mu$M of caged IP3 caused a higher $Ca^{2+}$ response and a small translocation. Only high IP3 concentrations that evoked a large and prolonged $Ca^{2+}$ increase were able to displace PLCδ1PH-GFP from the plasma membrane. In contrast, BK stimulation caused a larger translocation response than the highest amounts of IP3 with a $Ca^{2+}$ signal that was comparable to that induced by the smallest amount of IP3 (FIG. 6A). In cells electroporated with no caged IP3 in the electroporation buffer, intense UV flashes did not influence intracellular $Ca^{2+}$ levels, membrane localization of the chimera, or any of the BK-induced changes herein described (not shown).

Next, the effects of interfering with PI(4, 5)P2 resynthesis on the kinetics of translocation in N1E-115 cells was studied. PI(4, 5)P2 resynthesis was inhibited by low concentrations (5 $\mu$M) of phenyl arsine oxide (PAO) (FIG. 6B) or quercetin (Wiedemann et al., *EMBO J.* 15:2094–2101 (1996)), or by depletion of free inositol using prolonged incubation in inositol-free medium (not shown). In PAO-treated cells, BK induced a sustained translocation of PLCδ1PH-GFP to the cytosol, while IP3 increases in such cells are only transient (Hunyady et al., *J. Biol. Chem.* 266:2783–2788 (1991)). In control experiments, these pretreatments did not influence signaling events such as BK-induced $Ca^{2+}$ signaling (peak $Ca^{2+}$ values of 870±130 nM in control cells, and 845±114 nM, in PAO pretreated cells, n=6, mean ±SEM) or the thrombin- and lysophosphatidate-induced actinomyosin contraction (Jalink et al., supra (1993); Jalink et al., *J. Cell Biol.* 118:411–419 (1992)). Similar observations were made in HEK293 cells (not shown), suggesting that the translocation of PH domains under these conditions reports the depleted PI(4, 5)P2 pool rather than the transient IP3 increase.

Figure 6:
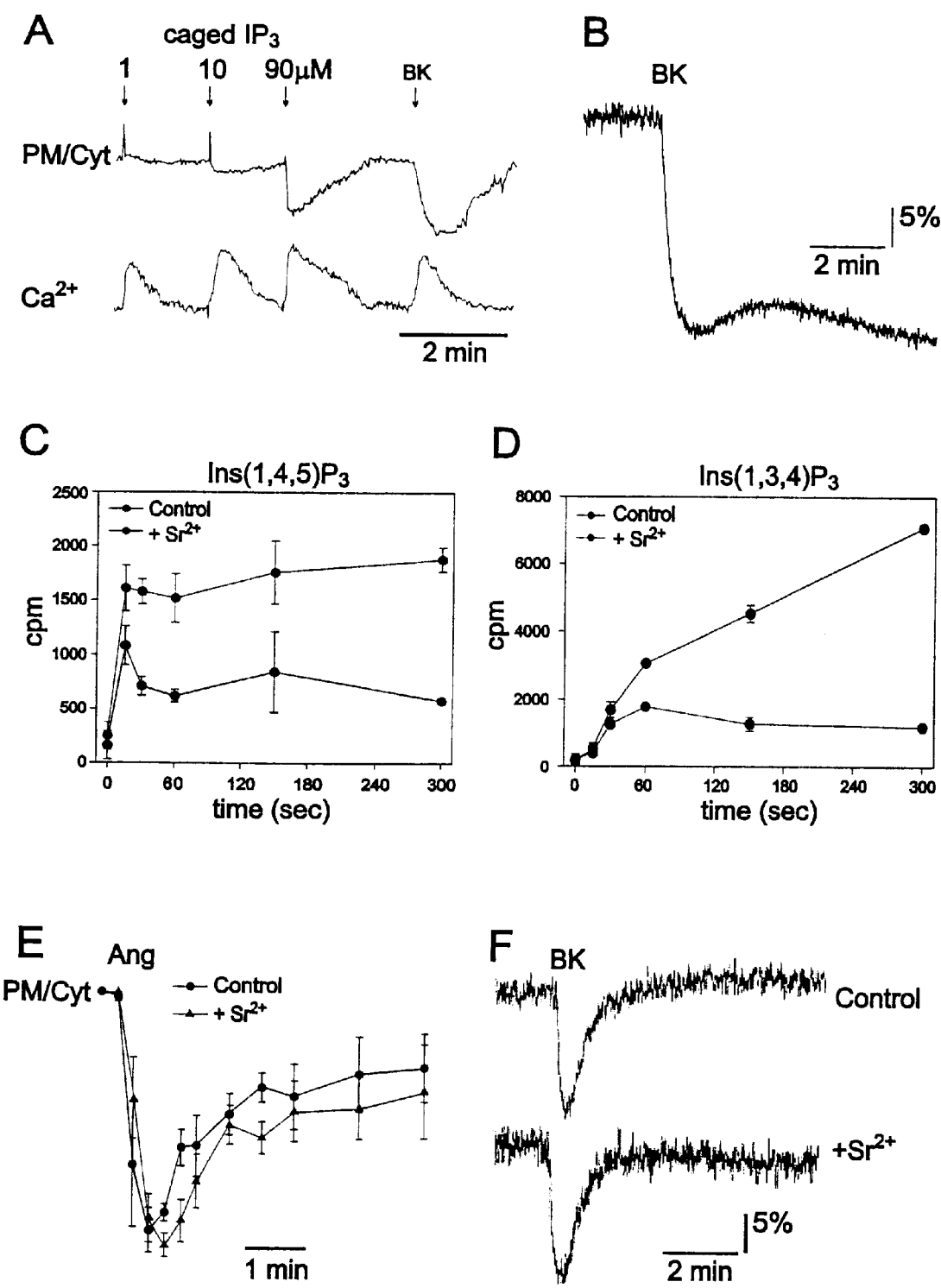
FIG. 6 shows that the PH domain of PLCδ1 reports changes in PI (4, 5)P2 rather than in IP3 in N1E-115 cells. (A) Cells expressing GFP-PH were loaded with both Fura-Red (20 FM) and caged IP3 (100 PM) by in-situ high frequency electroporation. Shown is the response of a single cell, assayed simultaneously for GFP translocation and $Ca^{2+}$ mobilization induced by flash photolysis of caged IP3. Arrows indicate photolysis of 1 μM, 10 μM and 90 μM. For comparison, bradykinin (1 μM) was added afterwards. Representative trace from 16 similar experiments. (B) FRET response to bradykinin detected in a single cell, pretreated with 5 μM of phenyl arsine oxide for 10 minutes. (C–D), time course of Ins (1, 4, 5)P3 and Ins (1, 3, 4)P3 formation in adrenal glomerulosa cells prelabeled with [$^3$H] inositol, after stimulation with angiotensin II (Ang, 1 μM) in the presence of 2 mM $Sr^{2+}$ or $Ca^{2+}$. (E) Angiotensin II-induced translocation as quantitated by analysis of serial confocal images of glomerulosa cells in the presence of $Sr^{2+}$ or $Ca^{2+}$. Data points represent means ±S.E.M., n=5. (F) Bradykinin-induced translocation, with and without $Sr^{2+}$, as detected by FRET in N1E-115 cells.

Moreover, when adrenal glomerulosa cells were stimulated with angiotensin II in the presence of $Sr^{2+}$, a condition under which IP3 metabolism via Ins(1, 3, 4, 5)P4 is greatly reduced (Balla et al., supra (1994)), hence yielding significantly higher Ins(1, 4, 5)P3- and diminished Ins(1, 3, 4)P3 increases (FIGS. 6 C,D), the translocation of PLCδ1PH-GFP was not significantly different (FIG. 6 E) from that observed in the presence of $Ca^{2+}$. Translocation responses of N1E-115 cells in response to BK were also similar in the presence of $Ca^{2+}$ or $Sr^{2+}$ (FIG. 6 F).

Taken together, these results indicate that, at least for the cells and agonists described above, PLCδ1PH-GFP translocation primarily reports changes in membrane PI(4, 5)P2 content and not IP3 increases. The reason for the apparently stronger binding of PLCδ1PH to membranes observed in live cells compared to the reported low in vitro affinity (Hirose et al., supra (1999)) to PIP2 containing lipid vesicles or BiaCore surface (Lemmon et al., *Proc. Natl. Acad. Sci. U.S.A* 92:10472–10476 (1995)) is unclear at present, but may indicate a more complex interaction of the PLCδ1PH domain with the native membranes that is not mimicked by the in vitro experiments. However, the finding reported in Hirose et al., supra (1999) that high IP3 levels can make significant contributions to the translocation response was confirmed. Whether such high levels or IP3 occur under the experimental conditions used with intact cells remains to be elucidated. Nevertheless, possible interference from large IP3 increases should be kept in mind during interpretations of the results of such translocation experiments.

FRET Reveals Response Heterogeneity to Different GPCR Agonists that is not Reflected in $Ca^{2+}$ Mobilization.

Having characterized the use of FRET between CFP and YFP-tagged PH domains of PLCδ1 to record PLC activation, the kinetics of responses to a set of calcium-mobilizing GPCR agonists were compared. Included in this panel were the peptide agonists BK and NKA, as well as the bioactive lipid lysophosphatidate (LPA), the protease thrombin, and the bioactive amine, histamine. Thrombin and LPA, in addition to inducing $Ca^{2+}$ mobilizations from internal stores, are also strong inducers of Rho-dependent remodeling of the actin cytoskeleton in these cells (Jalink et al., supra (1993); Jalink et al., supra (1992)). Histamine, on the other hand, does not induce Rho-dependent actin remodeling, but is known to induce $Ca^{2+}$ oscillations in several cell types (e.g. Paltauf-Doburzynska et al., *J. Physiol.* (Lond) 524 Pt.3:701–713 (2000); Zhu et al., *J. Biol. Chem.* 275:6063–6066 (2000))

Figure 7:
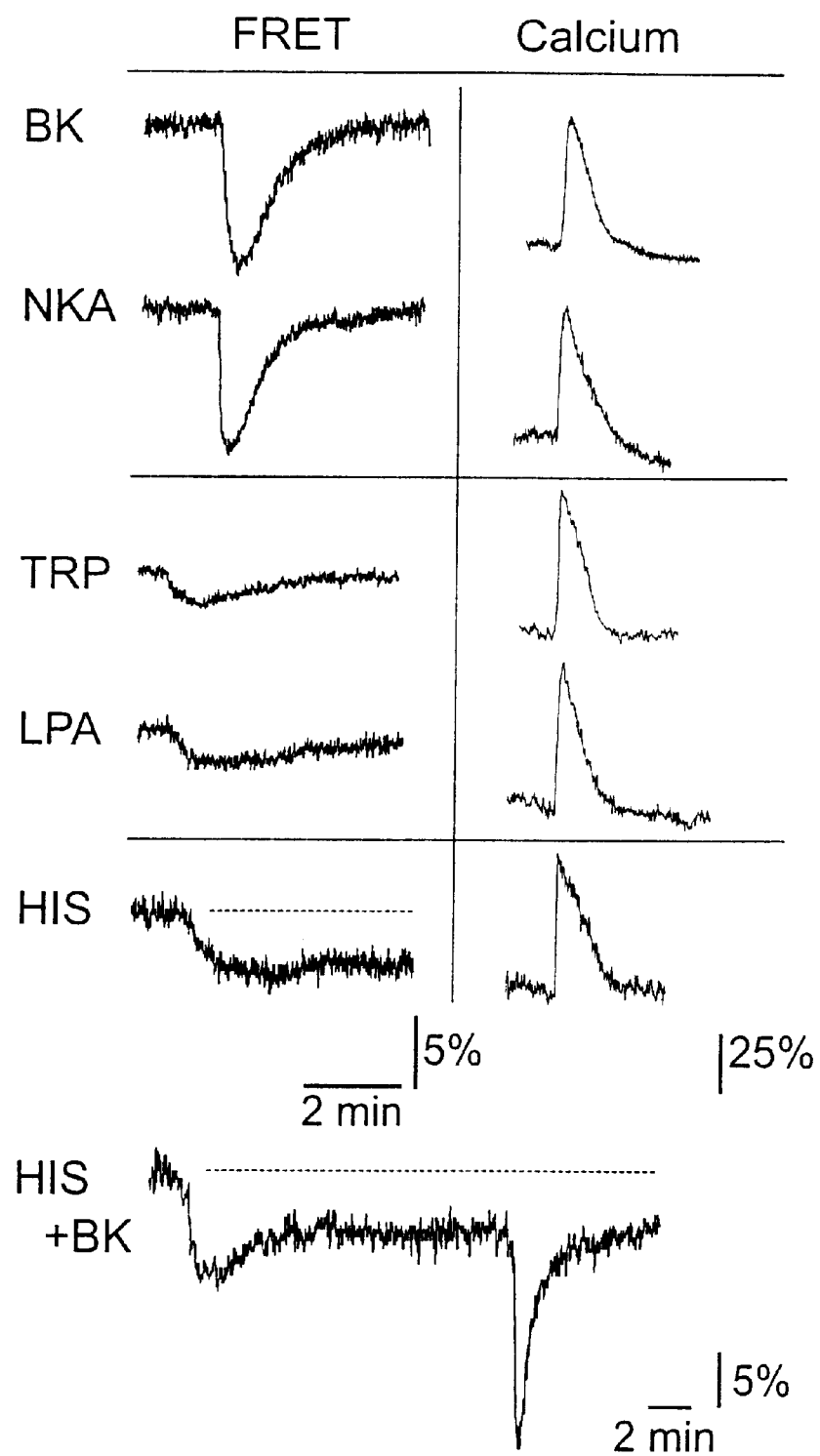
FIG. 7 shows heterogeneity of PLC activation responses to different GPCR agonists. Single N1E-115 cells expressing CFP-PH and YFP-PH were stimulated with 1 μM bradykinin (BK), 1 μM neurokinin A (NKA), 50 μM thrombin-receptor activating peptide (TRP), 1 μM lysophosphatidate (LPA) or 10 μM histamine (HIS). PLC activation as assayed by FRET, and intracellular $Ca^{2+}$ recordings for these agonists detected ratiometrically using Yellow Cameleon 2.1 in separate experiments, are shown. Changes in fluorescence ratio are expressed as percent of resting values. Shown are representative examples of experiments performed at least 10 times.

These agonists evoke very similar $Ca^{2+}$ mobilizations in N1E-115 cells, characterized by a fast onset and rapid termination well within 2 minutes (FIG. 7). Estimated peak $Ca^{2+}$ levels ranged from 0.6–2 $\mu$M, and, again, showed no consistent differences between agonists. When PLC activation patterns were recorded by FRET analysis, using the same agonists under identical conditions, several distinct profiles of PLC activation kinetics were obtained (FIG. 7). First, both NKA and BK caused fast and near-complete translocation of the probe. This response was transient, returning to baseline within 2–5 minutes. Stimulation with thrombin or LPA evoked a different type of response: these translocations had slower onset and smaller amplitude, averaging 25% of BK response control values (n=22). They also returned to baseline at a slower rate. The response to histamine was much slower and of small amplitude (40% of BK-induced peak values, n=15), but it was long-lasting (at least for 15 minutes, but often much longer).

Differences in degree of PIP2 hydrolysis induced by activation of different Gq-coupled receptors have also been reported (van der Bend et al., supra (1992), Tilly et al., *Biochem. J.* 266:235–243 (1990)) in biochemical studies. However, so far only cytosolic $Ca^{2+}$ responses could be used to analyze receptor activation patterns at the single cell level. On the other hand, the shape of the $Ca^{2+}$ response is determined by several other factors: it can be triggered at relatively low levels of IP3 and its shape is also determined by the $Ca^{2+}$-induced $Ca^{2+}$ release and inactivation properties of the IP3-receptor-channels, as well as by the activities of the various $Ca^{2+}$ sequestration mechanisms. The present approach provides an opportunity to study a more upstream receptor-mediated event, namely PLC activation, and its regulation in detail at the single cell level. PH Domain Translocation Kinetics Mirror Receptor Activation.

Figure 8:
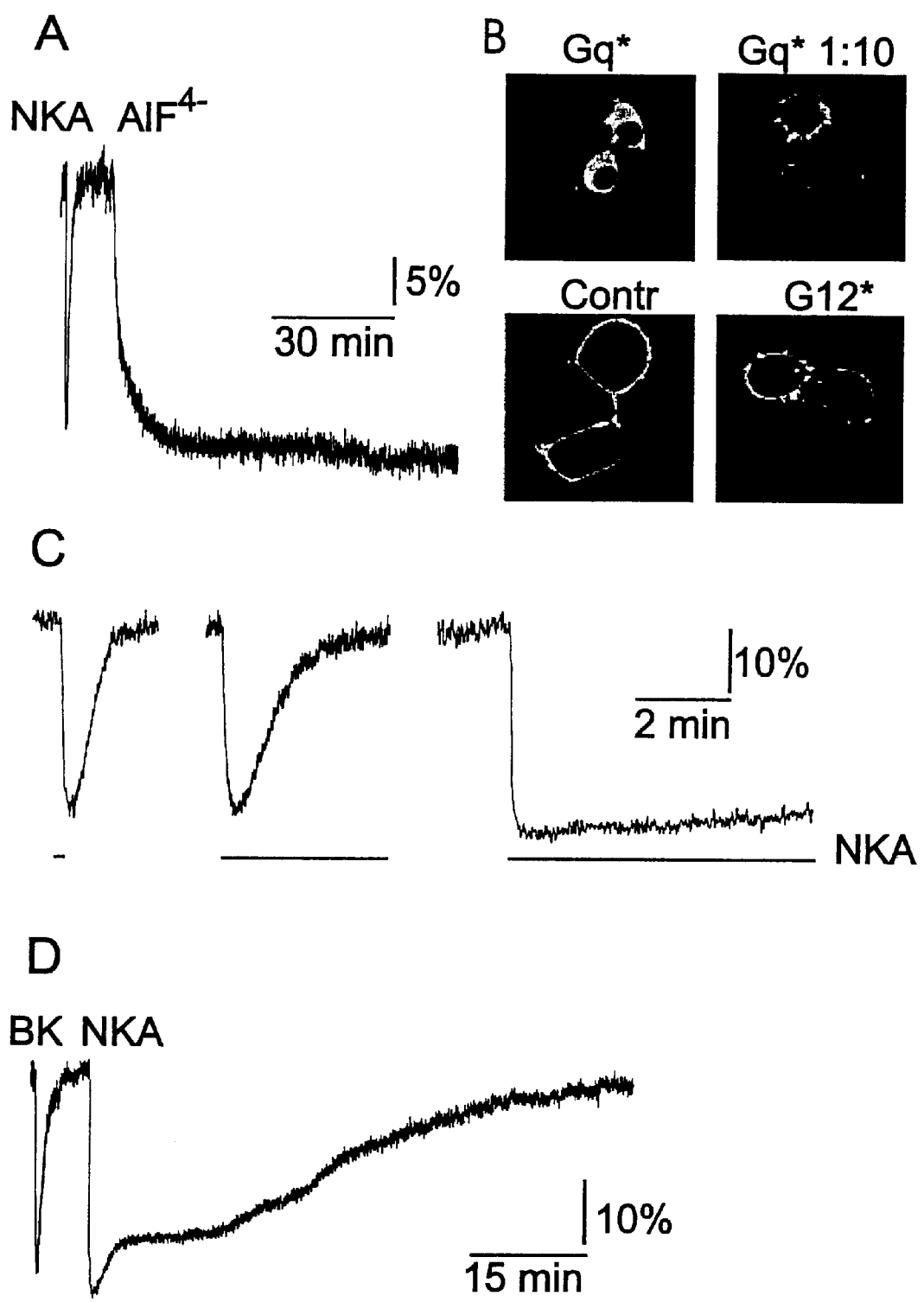
FIG. 8 shows that PLC inactivation kinetics mirror receptor inactivation. (A) FRET recording from a single N1E-115 cell stimulated with neurokinin A (NKA) and with 1 mM aluminum fluoride ($AlF^{4-}$). (B) Confocal micrographs of cells, taken 56 hours after transfection with PLCδ1PH-GFP (5 μg DNA/well) together with different amounts of constitutively active Gαq subunit (Gq*, 0.8 μg/well, and Gq* 1:10, 0.08 μg/well) or with constitutively active Gα12 at 0.8 μg/well (G12*). (C) PLC activation detected by FRET in single neuroblastoma cells (left panel), expressing wild-type NKA receptors, stimulated with 10 second pulse from a puffer pipette with 100 μg NKA; and cells stimulated by prolonged addition of NKA (1 μM) to the medium, expressing either wild-type receptors (middle panel) or a mutant truncated at its C-terminus (right panel). Recordings are all to the same scale. (D) Kinetics of PLC activation by NKA in a N1E-115 cell transfected with the C terminally truncated NK2 receptors on an extended time scale.

These results thus suggest that PLC activation as assessed by FRET is a more faithful index of receptor activity than the more distal $Ca^{2+}$ transients. However, inactivation could occur at various steps in the signal cascade, including at the levels of receptor, G protein and PLC and, conceivably, also by modulation (upregulation) of PI(4, 5)P2 resynthesis. To test whether there is desensitization at the level of PLC, G proteins were directly activated using $AlF^{4-}$ (FIG. 8A). While onset of $AlF^{4-}$ induced PLC activation was slow, no desensitization was observed in any of these experiments. Similarly, cells expressing a constitutively active Gαq mutant showed mostly cytosolic localization of PLCδ1 PH-GFP domains for at least 2 days (FIG. 8B). Control transfection with activated Gα12 had no effect. At lower expression levels, the activating mutant Gαq induced sustained partial translocation that also persisted for several days. These experiments suggested that no significant desensitization occurs downstream of Gq and PLC. In line with this notion, significant heterologous desensitization between sequentially added agonists was not observed (compare e.g. FIGS. 5 and 7, last panel), whereas prolonged exposure of cells to each individual agonist induced complete (homologous) desensitization.

To further determine whether such monitoring of PLC activity truly follows receptor activity (in other words coupling and uncoupling between receptors and G proteins), the FRET responses of N1E-115 cells expressing either the wild-type NK2 receptors or a C-terminally truncated form, which is greatly impaired in its ability to desensitize (Alblas et al., *J. Biol. Chem.* 270: 8944–8951 (1995)), were compared. After stimulation of the wild-type human NK2 receptors the translocation response decays towards baseline within minutes (average 50%) recovery time 83±38 s, n=25; compare FIGS. 7 and 8C). Application of short pulses of agonist using a puffer pipette resulted in incomplete desensitization, and decayed significantly faster (45±7 s, n=60, FIG. 8C) between applications of stimuli due to the rapid dissociation of the ligand from the receptor (Vollmer et al., *J. Biol. Chem.* 274:37915–37922 (1999)). Conversely, stimulation of a C-terminally truncated mutant human NK2 receptor, that was reported to be transforming in Rat-1 fibroblasts, and which has been found to display prolonged coupling to PLC (Alblas et al., supra (1995); Alblas et al., EMBO J. 15:3351–3360 (1996); Alblas et al., *J. Biol. Chem.* 268:22235–22238 (1993)) induced a much prolonged cytosolic translocation as assessed in FRET analysis (FIG. 8C). However, in the majority of cells, the FRET signal eventually slowly returned to baseline (FIG. 8D; note the different time scale), with an average 50% recovery time of 1365±599 s (n=19) in the truncated receptor. This result indicates the existence of an alternative and much slower desensitization mechanism that functions even in NK2 receptors lacking the C-terminus. The kinetics of this slow desensitization closely paralleled those of receptor internalization (not shown), suggesting that one of the main determinants for termination of NKA-induced PLC signaling could be receptor internalization. Analysis of receptor activity by monitoring PLC activity by FRET will greatly aid further studies addressing these questions in more detail.

In summary, described above is a fluorescence resonance-based detection scheme of membrane localization of tagged PLCδ1PH domains for analysis of activation-inactivation kinetics of PLC in single cells with high temporal resolution. This method has a number of significant advantages over confocal detection of membrane localization, including: (i) a significant decrease in excitation intensity allowing prolonged experiments or very fast sampling with little photobleaching and phototoxicity; (ii) suitability for very flat cells such as fibroblasts and motile cells; (iii), extendibility to record from cell populations as well as from small subregions such as neurites; and (iv) a simpler detection hardware. FRET detection of PLC activation is a fairly robust response that can be routinely obtained in a variety of cell types.

Analysis of the translocation responses suggests that localization of PLCδ1PH-GFP largely reports PI(4, 5)P2 dynamics, although at high concentrations IP3 can also contribute to translocation of the PH domains to the cytosol. Comparison of the $Ca^{2+}$ and FRET-recorded responses of several agonists of GPCRs suggest that PLC activation detected by FRET is a more faithful reflection of receptor activity than the $Ca^{2+}$ signal and that little if any "desensitization" or "uncoupling" occurs beyond the levels of G proteins.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention.

What is claimed is:

1. A phosphatidylinositol 4,5-bisphosphate (PIP2) indicator, said indicator comprising:
   (a) a first polypeptide comprising:
      (i) a pleckstrin homology (PH) domain; and
      (ii) a donor fluorescent domain
   (b) a second polypeptide comprising:
      (i) a pleckstrin homology (PH) domain; and
      (ii) an acceptor fluorescent domain;
         wherein fluorescence resonance energy transfer (FRET) between said donor domain and said acceptor domain indicates PIP2 levels.

2. The indicator of claim 1, wherein said PH domain is a PLCδ1 or PLCβ PH domain.

3. The indicator of claim 1, wherein said donor fluorescent domain is selected from the group consisting of a GFP and a dsRED.

4. The indicator of claim 1, wherein said donor fluorescent domain is a CFP.

5. The indicator of claim 1, wherein said acceptor fluorescent domain is selected from the group consisting of a GFP and a dsRED.

6. The indicator of claim 1, wherein said acceptor fluorescent domain is a YFP.

7. A cell comprising the indicator of claim 1.

8. A nucleic acid kit, the nucleic acid molecule components of which encode a PIP2 indicator, said indicator comprising:
   (a) a first polypeptide comprising:
      (i) a PH domain; and
      (ii) a donor fluorescent domain
   (b) a second polypeptide comprising:
      (i) a PH domain; and
      (ii) an acceptor fluorescent domain;
         wherein fluorescence resonance energy transfer (FRET) between said donor domain and said acceptor domain indicates PIP2 levels.

9. The kit of claim 8, wherein said PH domain is a PLCδ1 or PLCβ PH domain.

10. The kit of claim 8, wherein said donor fluorescent domain is selected from the group consisting of a GFP and a dsRED.

11. The kit of claim 8, wherein said donor fluorescent domain is a CFP.

12. The kit of claim 8, wherein said acceptor fluorescent domain is selected from the group consisting of a GFP and a dsRED.

13. The kit of claim 8, wherein said acceptor fluorescent domain is a YFP.

14. A cell expressing the nucleic acid molecule components of the kit of claim 8.

15. A method of indicating PIP2 levels in a cell, comprising:
   (a) providing a cell containing the PIP2 indicator of claim 1; and
   (b) determining FRET between said donor fluorescent domain and said acceptor fluorescent domain,
      wherein FRET between said donor domain and said acceptor domain indicates PIP2 levels in the cell.

16. The method of claim 15, wherein said PH domain is a PLCδ1 or PLCβ PH domain.

17. The method of claim 15, wherein said donor fluorescent domain is selected from the group consisting of a GFP and a dsRED.

18. The method of claim 15, wherein said donor fluorescent domain is a CFP.

19. The method of claim 15, wherein said acceptor fluorescent domain is selected from the group consisting of a GFP and a dsRED.

20. The method of claim 15, wherein said acceptor fluorescent domain is a YFP.

21. The method of claim 15, wherein said cell recombinantly expresses a G-protein coupled receptor.

22. A method of identifying a compound that modulates PIP2 levels in a cell, comprising:
   (a) contacting a cell containing the PIP2 indicator of claim 1 with one or more test compounds; and
   (b) determining FRET between said donor fluorescent domain and said acceptor fluorescent domain following said contacting,
      wherein increased or decreased FRET following said contacting indicates that said test compound is a compound that modulates PIP2 levels in the cell.

23. The method of claim 22, wherein said PH domain is a PLCδ1 or PLCβ PH domain.

24. The method of claim 22, wherein said donor fluorescent domain is selected from the group consisting of a GFP and a dsRED.

25. The method of claim 22, wherein said donor fluorescent domain is a CFP.

26. The method of claim 22, wherein said acceptor fluorescent domain is selected from the group consisting of a GFP and a dsRED.

27. The method of claim 22, wherein said acceptor fluorescent domain is a YFP.

28. The method of claim 22, wherein said contacting is by administration of said test compound to the exterior of said cell.

29. The method of claim 22, wherein said contacting is by recombinant expression of said test compound in said cell.

30. The method of claim 22, wherein said cell recombinantly expresses a G-protein coupled receptor.

* * * * *